(12) United States Patent
Hatamian et al.

(10) Patent No.: US 11,389,376 B2
(45) Date of Patent: Jul. 19, 2022

(54) WEARABLE INTRAVENOUS FLUID DELIVERY SYSTEM

(71) Applicant: Mediccene Inc., Mission Viejo, CA (US)

(72) Inventors: Mehdi Hatamian, Mission Viejo, CA (US); Mehrtash Ghalebi, Irvine, CA (US)

(73) Assignee: Mediccene Inc., Mission Viejo, CA (US)

(*) Notice: Subject to any disclaimer, the term of this patent is extended or adjusted under 35 U.S.C. 154(b) by 0 days.

(21) Appl. No.: 17/557,889

(22) Filed: Dec. 21, 2021

(65) Prior Publication Data

US 2022/0192922 A1 Jun. 23, 2022

Related U.S. Application Data

(60) Provisional application No. 63/128,738, filed on Dec. 21, 2020.

(51) Int. Cl.
| | |
|---|---|
| *A61J 1/12* | (2006.01) |
| *A61M 5/14* | (2006.01) |
| *A61J 1/14* | (2006.01) |
| *A61M 5/168* | (2006.01) |

(52) U.S. Cl.
CPC ............ *A61J 1/12* (2013.01); *A61J 1/1468* (2015.05); *A61M 5/1409* (2013.01); *A61M 5/1415* (2013.01); *A61M 5/16827* (2013.01); *A61J 2205/00* (2013.01); *A61M 2005/1416* (2013.01)

(58) Field of Classification Search
CPC ............ A61M 5/14244; A61M 39/10; A61M 5/1407; A61M 5/1411; A61M 5/1414; A61M 39/105
See application file for complete search history.

(56) References Cited

U.S. PATENT DOCUMENTS

| | | | |
|---|---|---|---|
| 5,492,533 A * | 2/1996 | Kriesel | A61M 5/1409 604/890.1 |
| 5,505,708 A * | 4/1996 | Atkinson | A61M 5/1486 604/410 |
| 6,969,031 B2 | 11/2005 | Ugent et al. | |
| 8,485,727 B2 * | 7/2013 | Trouilly | A23L 33/10 206/219 |
| 2009/0095783 A1 | 4/2009 | Price | |

(Continued)

*Primary Examiner* — Brandy S Lee
(74) *Attorney, Agent, or Firm* — Makoui Law, PC; Ali Makoui

(57) ABSTRACT

An intravenous (IV) fluid delivery system include an IV bag and a fluid delivery device. The IV bag is made of many fluidic channels that keep the fluid distributed across the bag such that the bag may be easily and comfortably wrapped around the arm and shoulder of a person. The fluid delivery device includes a processor controlled electromechanical delivery mechanism that controls a positive displacement pump. The pump moves the fluid into a tube and a needle that is connected to a person's vein. The processor repeatedly turns the pump on or off to gradually transfer the fluid from the IV bag into the person's vein. The processor controls the granularity of the fluid delivery, where the fluid may be administered in a fluid delivery period, the fluid delivery may then be stopped in a subsequent fluid stoppage period, followed by other fluid delivery periods.

20 Claims, 15 Drawing Sheets

(56) References Cited

U.S. PATENT DOCUMENTS

2012/0132784 A1 5/2012 Dukes et al.
2015/0320929 A1 11/2015 Simonds
2020/0324042 A1 10/2020 King et al.

* cited by examiner

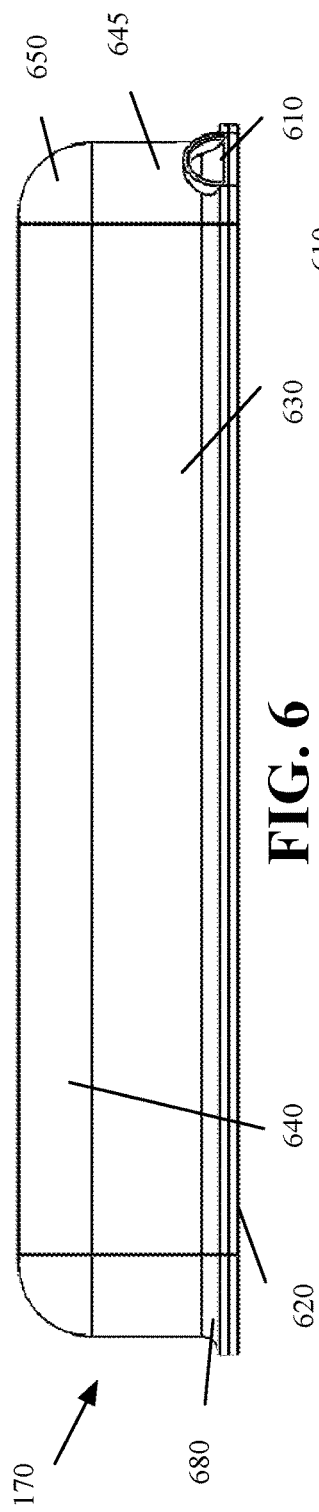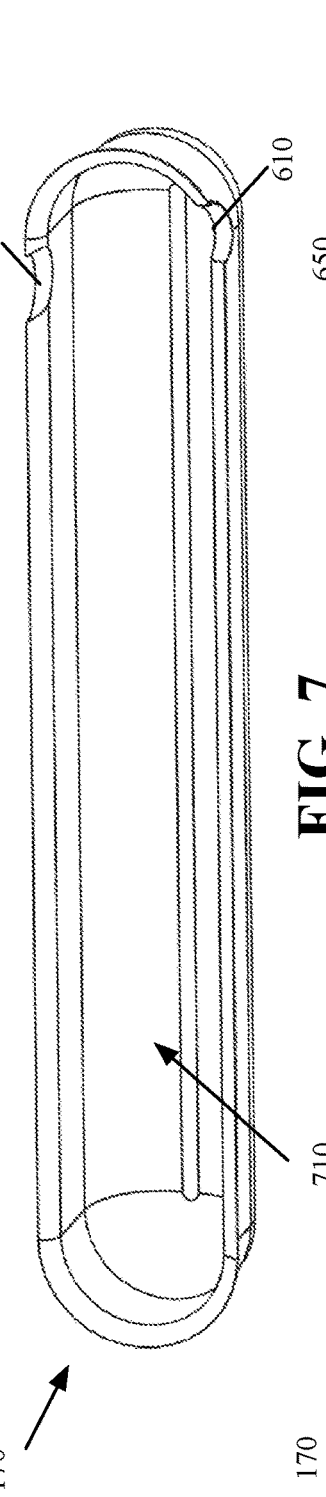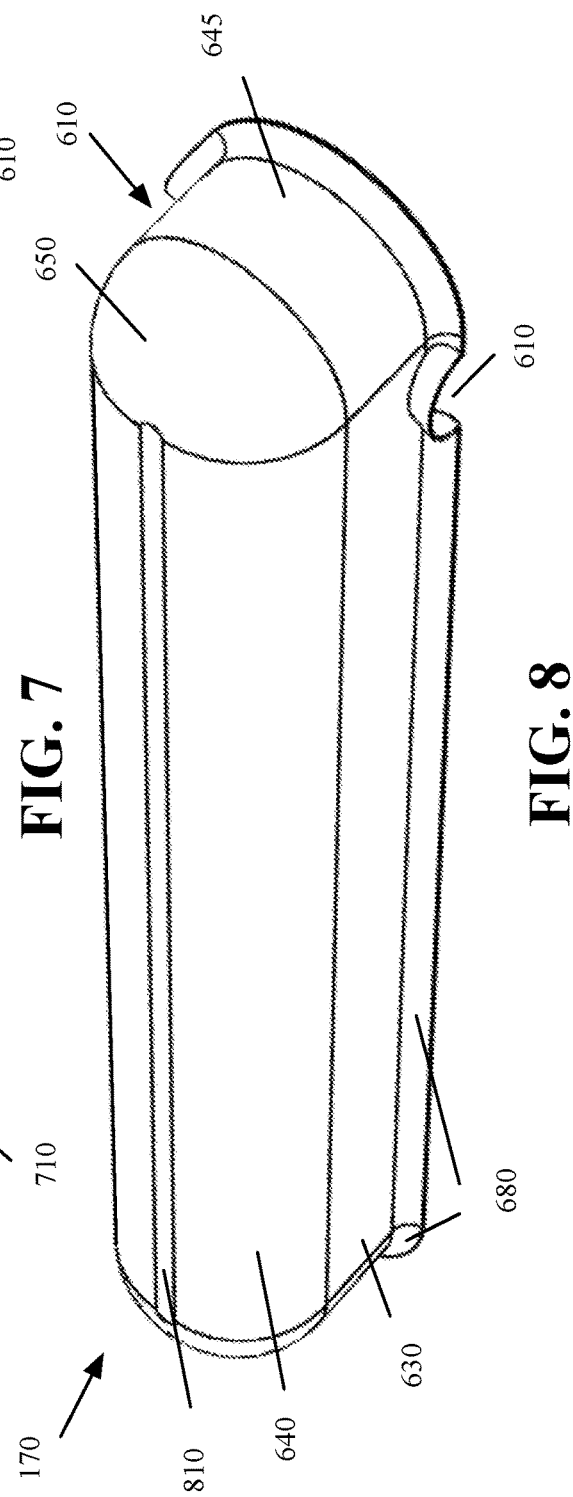

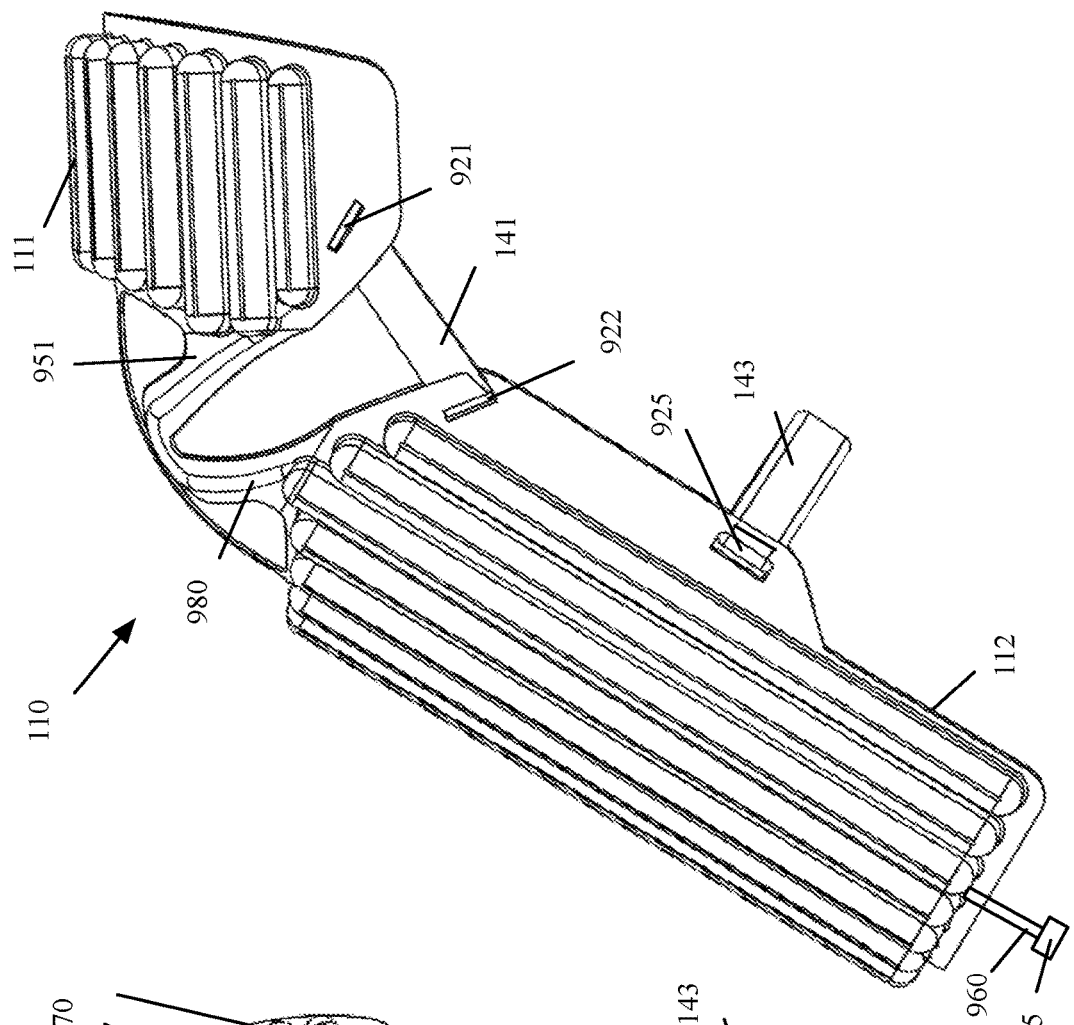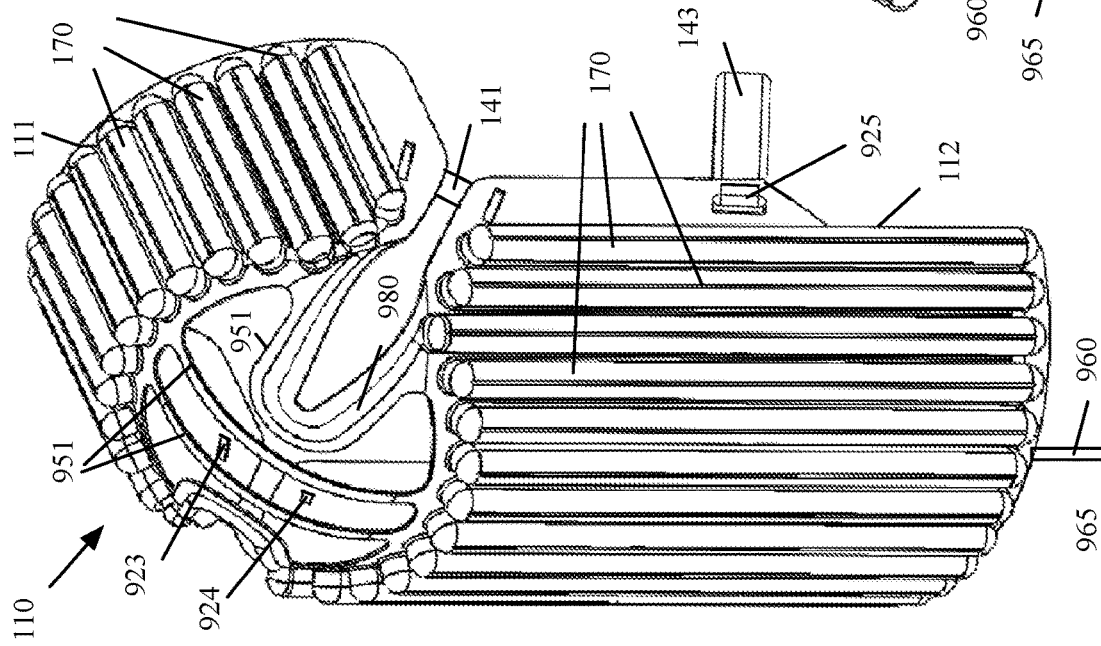

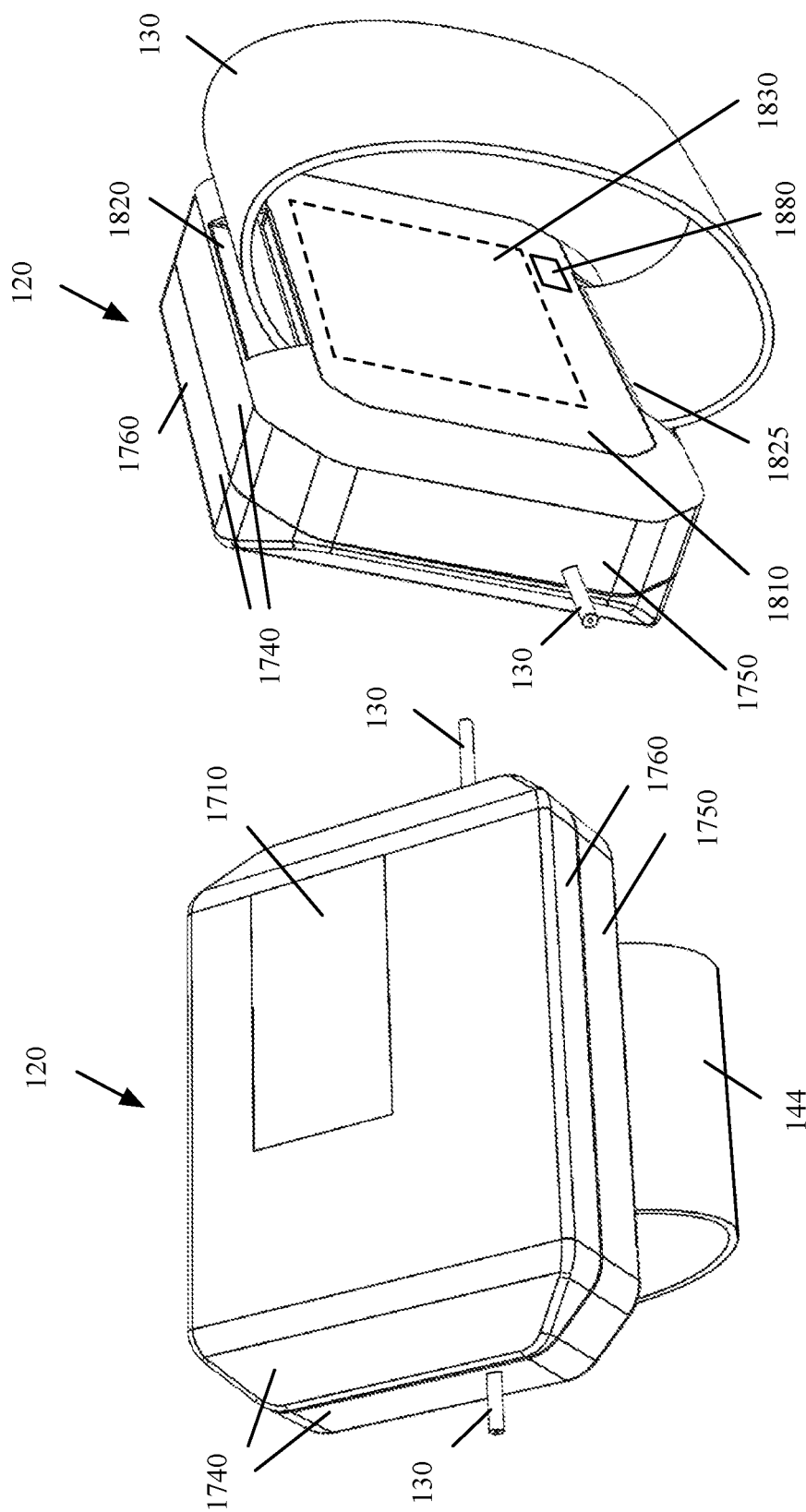

WEARABLE INTRAVENOUS FLUID DELIVERY SYSTEM

CLAIM OF BENEFIT TO PRIOR APPLICATIONS

This application claims the benefit of U.S. Provisional Patent Application Ser. No. 63/128,738, filed on Dec. 21, 2020. The contents of U.S. Provisional Patent Application 63/128,738 are hereby incorporated by reference.

BACKGROUND

Intravenous (IV) therapy is widely used to deliver fluids such as medications and nutrition directly into a person's vein. The IV therapy may be used to administer medications, blood products, electrolytes, or nutrition. Equipment used for IV therapy includes a bag, referred to as IV bag, and sterile tubing through which the fluid is administered. The IV bag is usually hanged at a height above the person and the solution in the bag is pulled via gravity through the tubing and a needle into a person's vein. Portable versions of IV bags include bulky devices that are worn as backpacks, fanny packs, or taut pockets, which are heavy, bulky, and, and inflexible.

BRIEF DESCRIPTION OF THE DRAWINGS

The various embodiments of the present wearable intravenous fluid delivery system now will be discussed in detail with an emphasis on highlighting the advantageous features. These embodiments depict the novel and non-obvious wearable intravenous fluid delivery system shown in the accompanying drawings, which are for illustrative purposes only. These drawings include the following figures, in which like numerals indicate like parts:

FIG. 6 is a side elevation view,

FIG. 7 is a bottom perspective view, and

FIG. 8 is a side perspective view of a fluidic channel of an IV bag, according to various aspects of the present disclosure;

FIG. 12 is a side perspective view of the IV bag illustrating the approximate shape of the IV bag when it is worn on the shoulder and arm of a person, according to various aspects of the present disclosure;

FIG. 13 is a side perspective view of an IV bag of FIG. 12, illustrating the approximate shape of the IV bag when the person raises the arm, according to various aspects of the present disclosure;

FIG. 17 is a top perspective view of a fluid delivery device, according to various aspects of the present disclosure;

FIG. 18 is the back perspective view of the fluid delivery device of FIG. 17, according to various aspects of the present disclosure;

DETAILED DESCRIPTION

Figure 1:
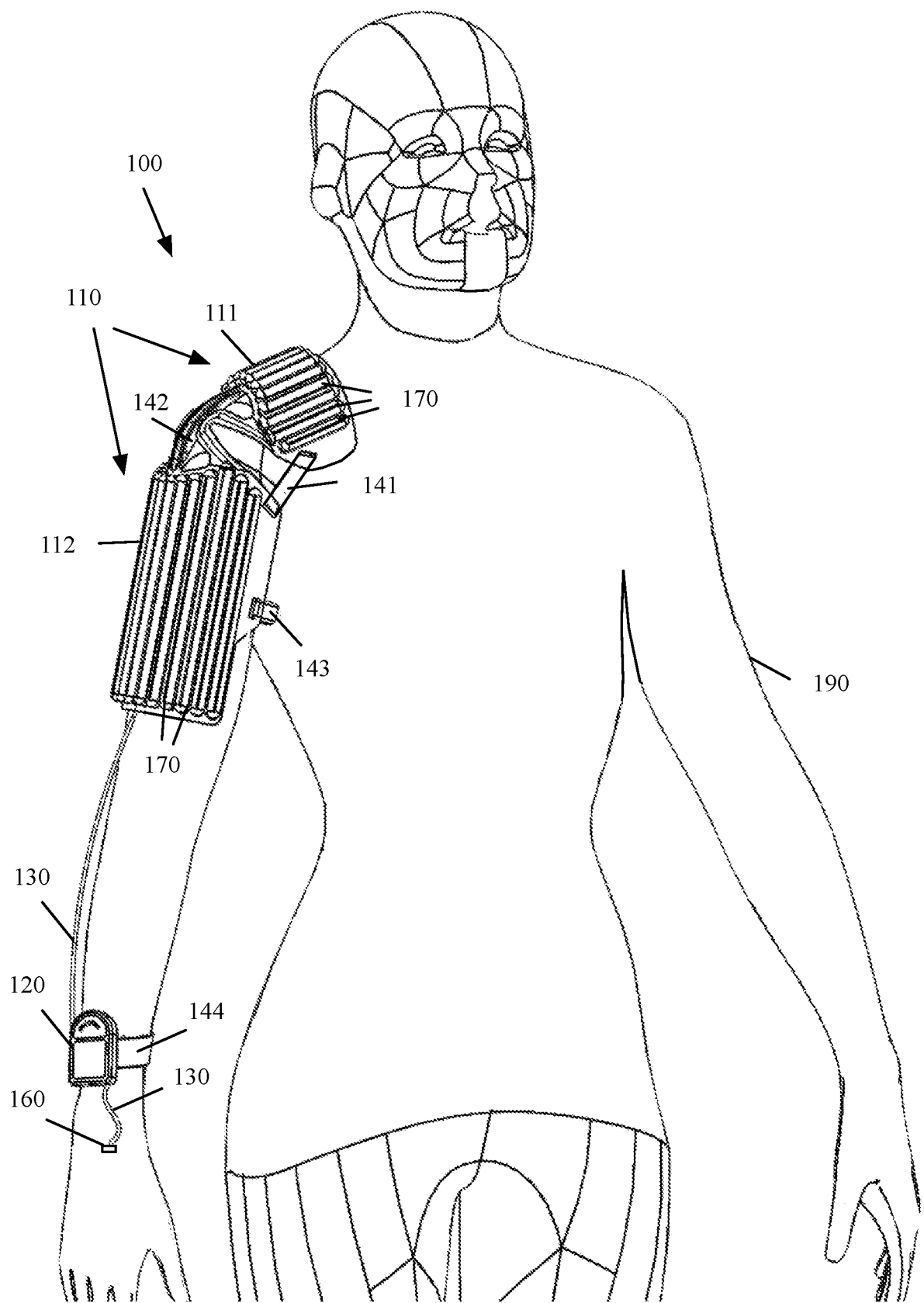
FIG. 1 illustrates a front perspective view.

One aspect of the present embodiments includes the realization that it is impractical to wear the existing IV bags over the shoulder of an active person to deliver fluids intravenously over a long period of time. The IV bags typically include a hollow bag that is made of a plastic, such as polyvinyl chloride (PVC). The bag becomes inflexible when it is filled with fluid. The filled bag becomes impractical to wear on the arm by itself. If the bag is attached to the arm with a harness, the overall size of the bag and the harness become large and cannot be worn under regular clothes. In addition, using a traditional IV bag as a wearable bag may cause a stoppage of fluid if the person, for example, lays down and applies pressure on the IV bag. When the IV bag is almost empty, there may be the risk of the fluid to seep back from the person's vein into the IV bag.

The present embodiments solve the aforementioned problems by providing an IV bag that may be made of many fluidic channels that keep the IV fluid distributed across the bag such that the bag may be easily and comfortably wrapped around the arm of a person, or be worn on the body (e.g., on the shoulder), without pinching the fluid or blocking the fluid flow.

Another aspect of the present embodiments includes the realization that the IV bag are hanged at a height above the person and the fluid in the bag is pulled via gravity through the tube and a needle into a person's vein and do not provide a granular control over the delivery of the fluid to the person. The existing portable IV bags also do not provide a granular control over the delivery of the fluid to the person.

Some of the present embodiments solve the aforementioned problem by providing an intravenous fluid delivery system that uses a processor controlled electromechanical delivery mechanism. The processor controls a positive displacement pump, such as a peristaltic pump or a reciprocating pump. The pump may be used to move the fluid from the IV bag into a tube and a needle that is connected to a person's vein. The processor may be configured to repeatedly turn the pump on or off, in order for the fluid to gradually be transferred from the IV bag, through the tube and the needle, into the person's vein. The processor may be configured not only to control the total fluid delivery time but also the granularity of the fluid delivery. The total fluid delivery time may be divided into smaller periods of fluid delivery and fluid stoppage, where the fluid may be administered in a fluid delivery period, the fluid delivery may then be stopped in a subsequent fluid stoppage period, followed by another fluid delivery period, etc. The individual fluid delivery periods and fluid stoppage periods are individually programmable and may have the same or different lengths.

The controlled mode delivery of the present embodiments allows for the flexibility of the step-by-step delivery of any type of drug in liquid form and provides the technical advantage of allowing the body to absorb a very small dose (e.g., a micro-dose) of the fluid before delivering the next dose. Each drug may have its own delivery duration and delivery rate requirements, which may be programmed into the intravenous fluid delivery system of the present embodiments. The programming may be done at the manufacture time, at the shipment time, or in the field. The programming in the field may be done either through a display that is integrated in the intravenous fluid delivery system or through an application program running on an external electronic device that is wirelessly connected to the intravenous fluid delivery system. The integrated display or the application program may provide a user interface with options to program the total duration of the fluid delivery, the number of fluid delivery and fluid stoppage periods, and the duration of each individual fluid delivery and fluid stoppage period. The programming provides control over the total duration of fluid delivery and the fluid delivery rate. The delivery rate may be programmed to stay constant by selecting the same amount of time for all fluid delivery periods and the same amount of time for all fluid stoppage periods. Alternatively, the fluid delivery and fluid stoppage periods may individually be programmed.

The remaining detailed description describes the present embodiments with reference to the drawings. In the drawings, reference numbers label elements of the present embodiments. These reference numbers are reproduced below in connection with the discussion of the corresponding drawing features.

Figure 2:
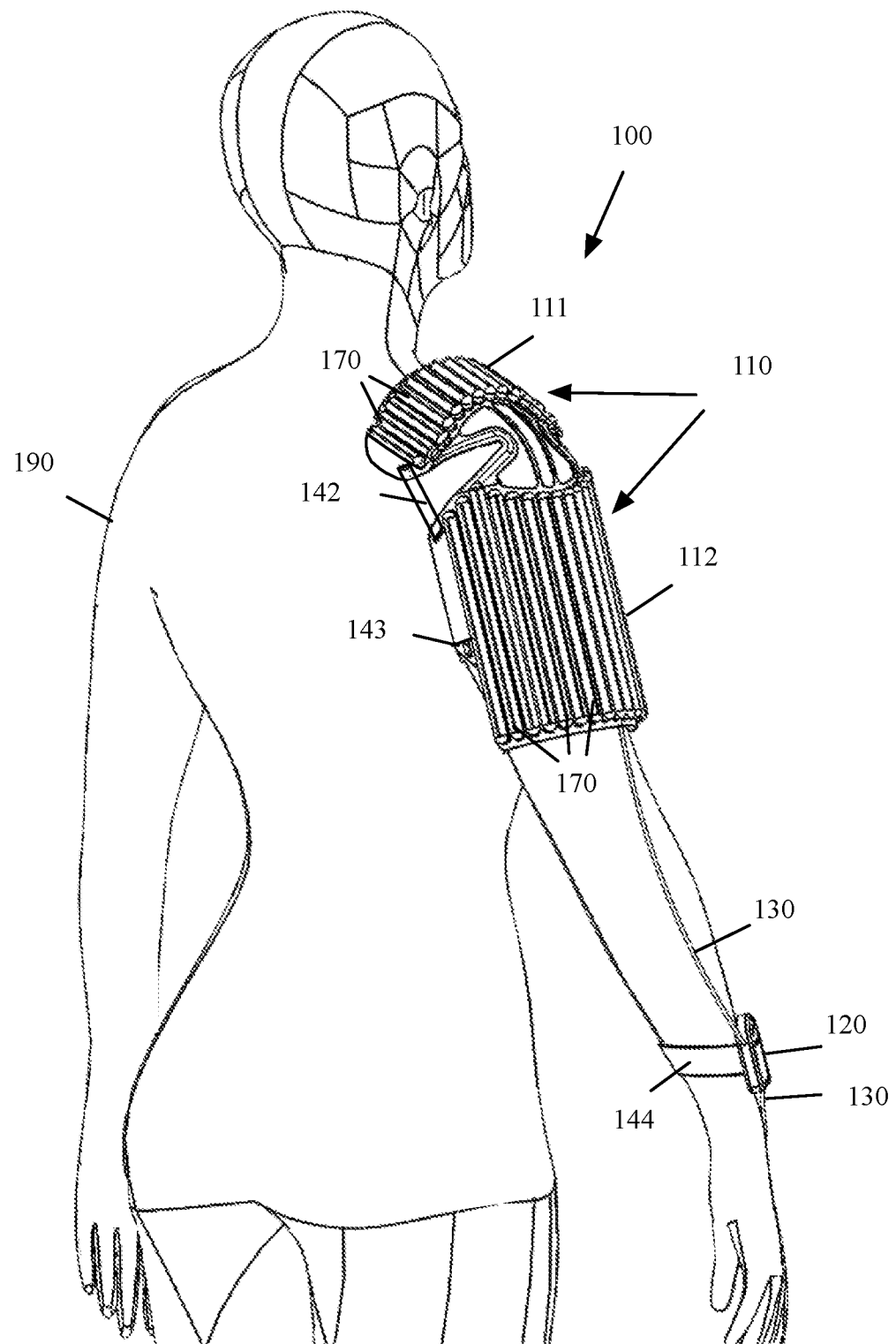
FIG. 2 illustrates a back perspective view of an example intravenous fluid delivery system with a wearable IV bag, according to various aspects of the present disclosure.
Figure 3:
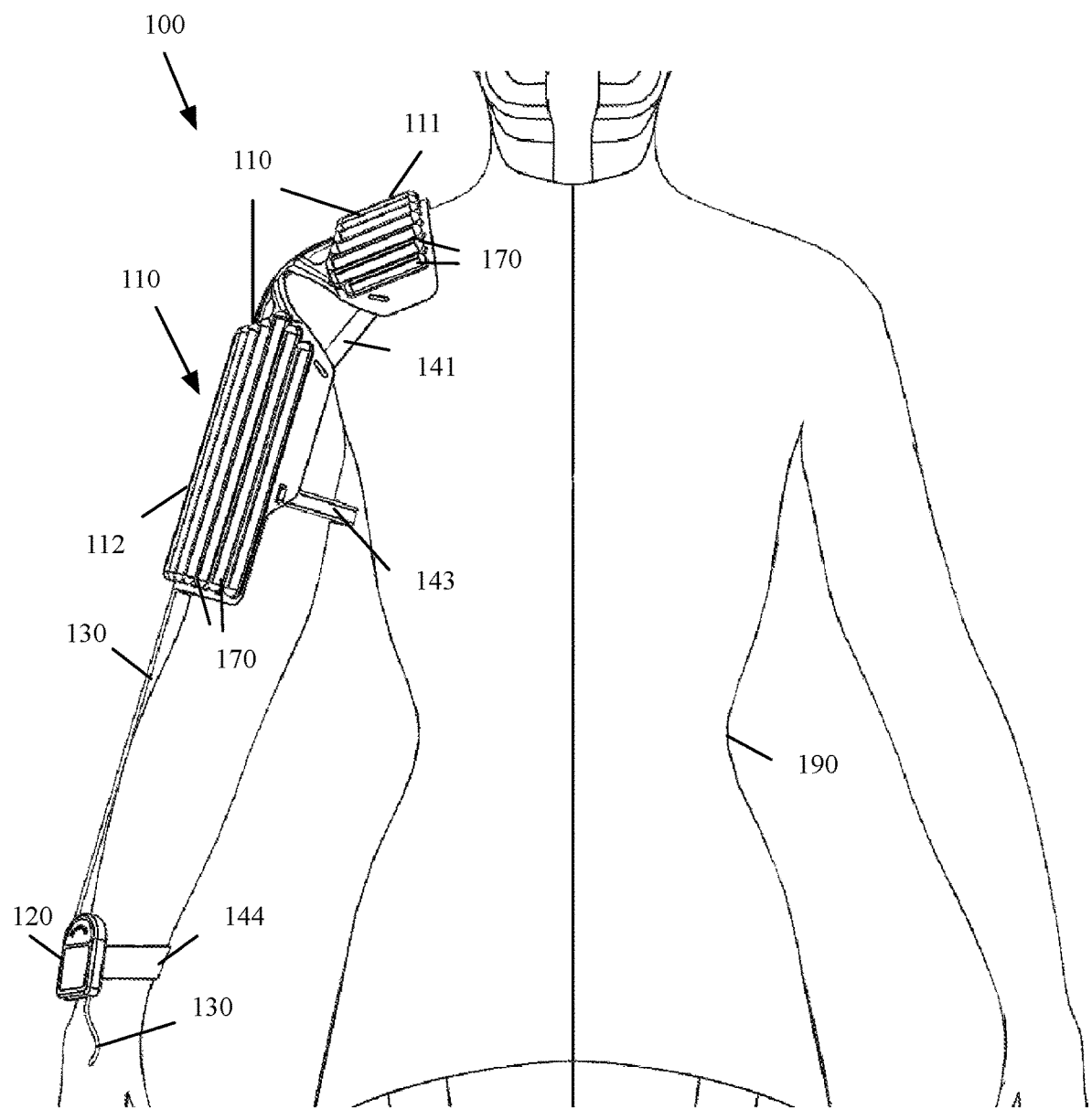
FIG. 3 illustrates a front elevation view.
Figure 4:
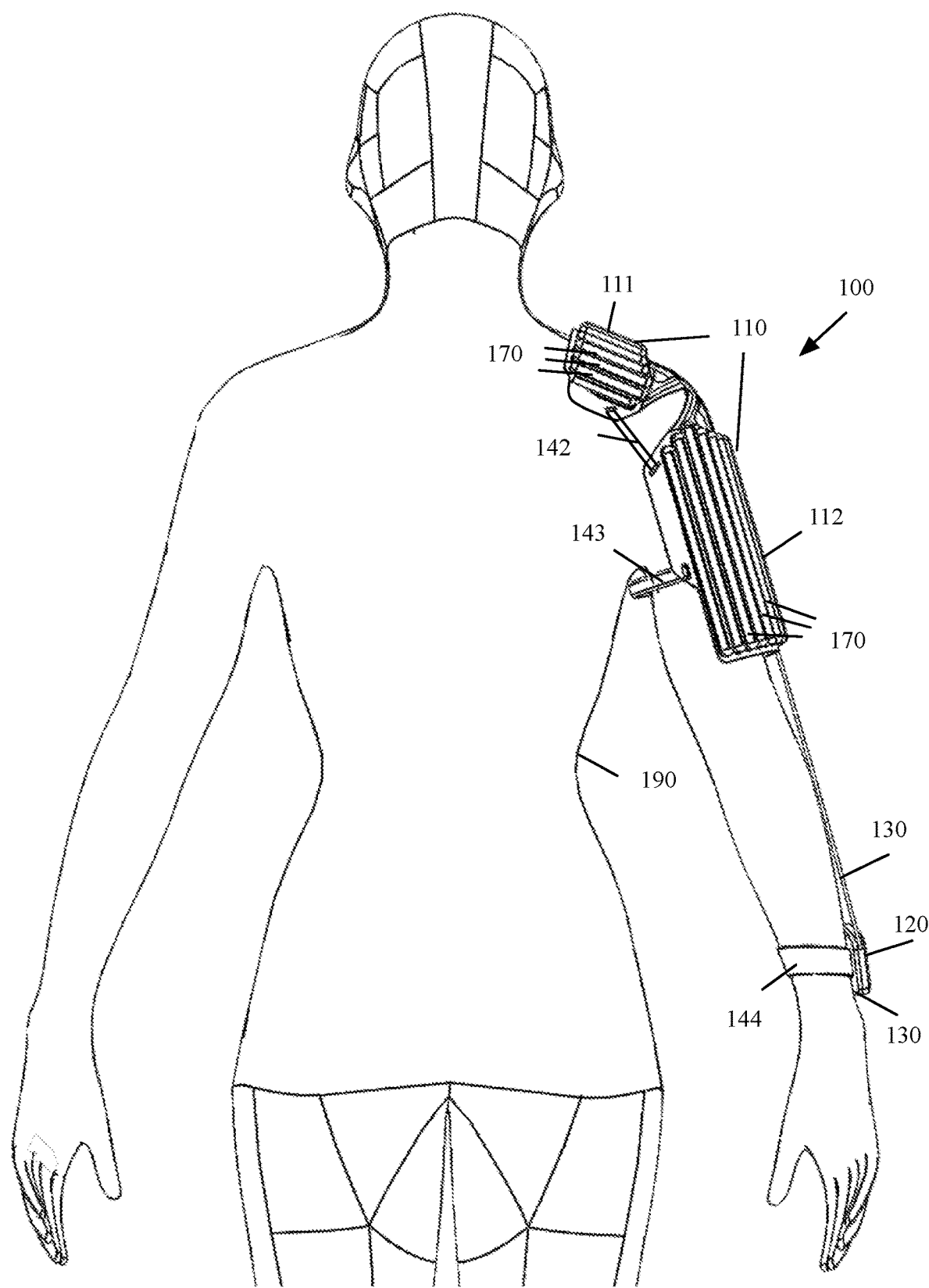
FIG. 4 illustrates a back elevation.
Figure 5:
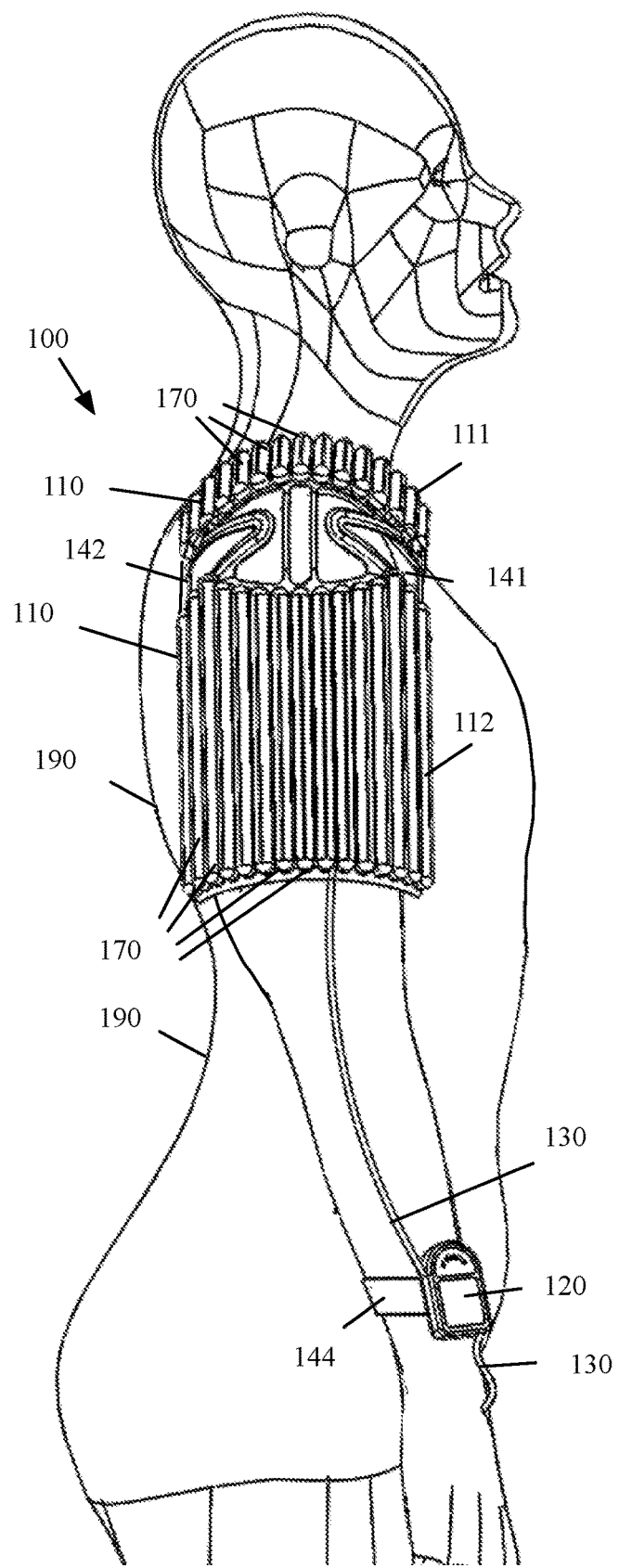
FIG. 5 illustrates a side elevation view of the intravenous fluid delivery system of FIGS. 1 and 2, according to various aspects of the present disclosure.

FIG. 1 illustrates a front perspective view and FIG. 2 illustrates a back perspective view of an example intravenous fluid delivery system with a wearable IV bag, according to various aspects of the present disclosure. FIG. 3 illustrates a front elevation view, FIG. 4 illustrates a back elevation, and FIG. 5 illustrates a side elevation view of the intravenous fluid delivery system of FIGS. 1 and 2, according to various aspects of the present disclosure.

The term fluid used in this disclosure refers to liquids and solutions, such as, for example, and without limitations, drugs as well as nutrition, sugar, saline solutions, or blood products (e.g., plasma) that may not typically be classified as drugs or medications. Example uses of the intravenous drug delivery system of the present embodiments include administrating antibiotics, saline solutions, nutrition, sugar, etc., through a person's vein. Accordingly, the terms fluid and drug may be used interchangeably in this disclosure. The intravenous drug delivery system of the present embodiments may be used at home, at work, in transit, or at a point of care.

With reference to FIGS. 1-5, the intravenous fluid delivery system 100 may include an IV bag 110, a fluid delivery device 120, and a fluid transfer tube 130. The fluid transfer tube 130 may go around the rotor of a peristaltic pump inside the fluid delivery device 120, and may be connected to a needle (such as a butterfly needle) 160 that may be secured to the wrist of the person 190. It should be noted that the person 190 is not a part of the intravenous fluid delivery system 100 and is shown to demonstrate how the intravenous fluid delivery system 100 may be worn by a person.

The IV bag may include a shoulder section 111 and an arm section 112. The shoulder section 111 and the arm section 112 may include many fluidic channels (or fluid compartments) 170. The multiple fluidic channels (or multiple fluid compartments) 170 allow the IV bag to have a flexible shape and to conform to the contours of a person's body. For clarity, only some of the fluidic channels 170 are labelled in the figures. Although the IV bag is shown to be worn on the right shoulder and the right arm, the IV bag 110 may be worn on the left shoulder and the left arm. In addition, as described below with reference to FIG. 22, some embodiments may include two fluidically connected IV bags 110 and 110-1 that may be worn on both sides of the body.

FIG. 6 is a side elevation view, FIG. 7 is a bottom perspective view, and FIG. 8 is a side perspective view of a fluidic channel of an IV bag, according to various aspects of the present disclosure. With reference to FIGS. 6-8, the fluidic channel 170 includes a hollow interior 710 that may store a quantity of fluid. The exterior of the fluidic channel 170, in different embodiments, may have different outlines. For example, in the depicted embodiments, the fluidic channel 170 has round surfaces 640 and 650 and substantially square surfaces 630 and 810. The fluidic channel 170 may include a base 620 and a transitional surface 680 that connects the base 620 to the surface 630. The fluidic channels 170 may be elongated hollow channels. A typical length of a fluidic channel 170 may be, for example, and without limitations, be between 1 inch to 9 inches. A typical diameter (or width) of a fluidic channel 170 may be, for example, and without limitations, be between 0.1 inch to 0.8 inches.

The fluidic channels 170 of the IV bag 110 (FIGS. 1-5) may be fluidically connected to each other through one or more tubes. The openings 610 are used to fluidically connect the fluidic channel 170 of FIGS. 6-8 to other fluidic channels 170 of the IV bag.

Figure 9:
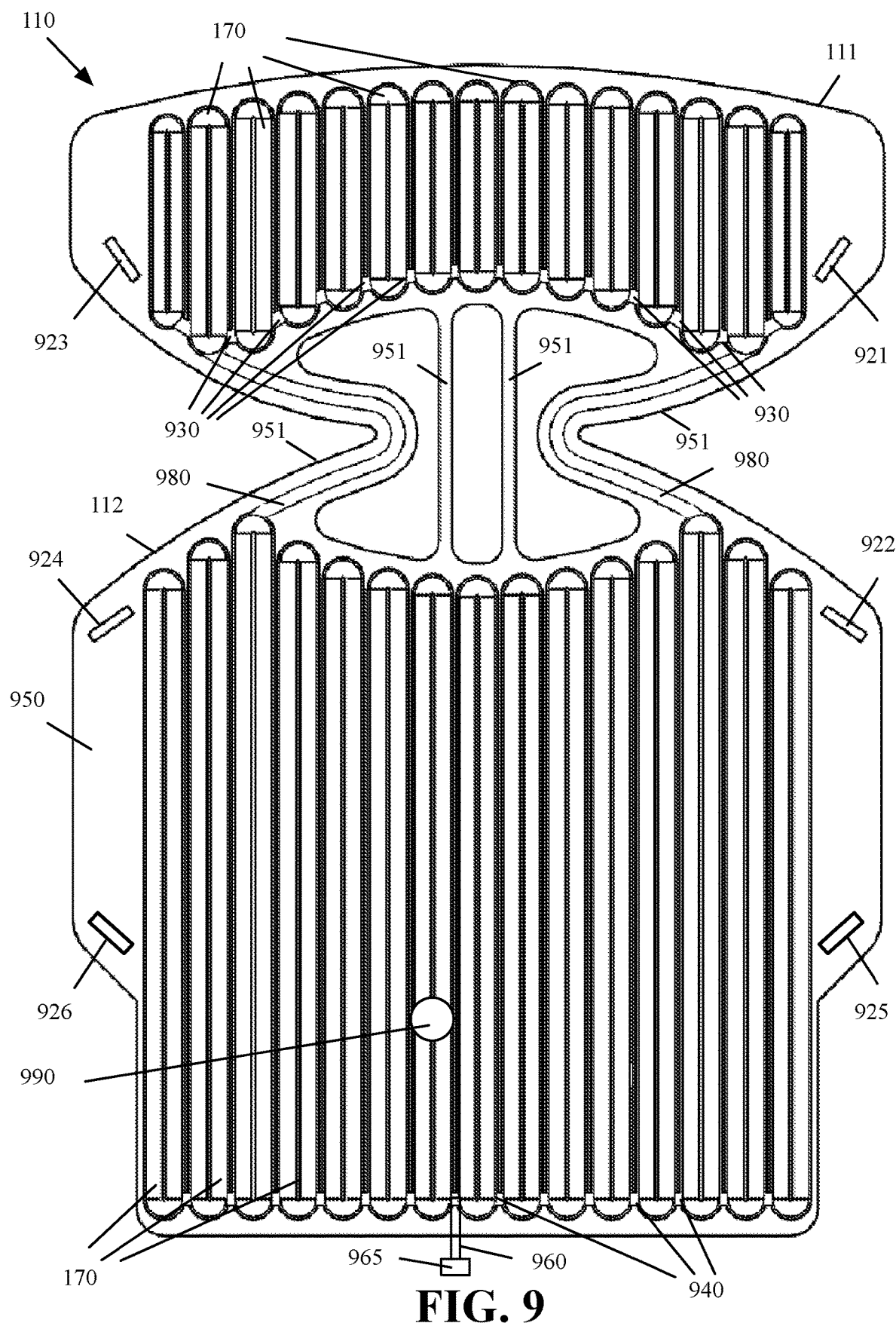
FIG. 9 is a front elevation view of an IV bag before being bent to be worn by a person, according to various aspects of the present embodiments.

FIG. 9 is a front elevation view of an IV bag before being bent to be worn by a person, according to various aspects of the present embodiments. With reference to FIG. 9, the fluidic channels 170 of the shoulder section 111 of the IV bag 110 may be fluidically connected to each other through one or more fluid passages (or tubes) 930. The fluidic channels 170 of the arm section 112 (FIGS. 1-5) of the IV bag 110 may be fluidically connected to each other through one or more tubes 940. For clarity, only some of the fluid passages 930 and 940 are labelled in the figures.

The fluidic channels 170 of the shoulder section 111 and the arm section 112 may be fluidically connected to each other by one or more tubes 980. Each tube 980 may pass through a connector 951. The IV bag 110 may include an output tube 960 and a connector 965 to connect the IV bag to the fluid delivery device 120 (FIGS. 1-5) through the fluid transfer tube 130. The IV bag 110 may include an injection port 990 to receive fluids other than those in the IV bag 110 may be injected into the IV bag 110, for example through a Y-set, a T-set, or a V-set connector. The Y-set, T-set, and V-set connectors are Y, T, and V shaped three-way connector set made of connecting plastic tubes used for delivering intravenous fluids.

Figure 10:
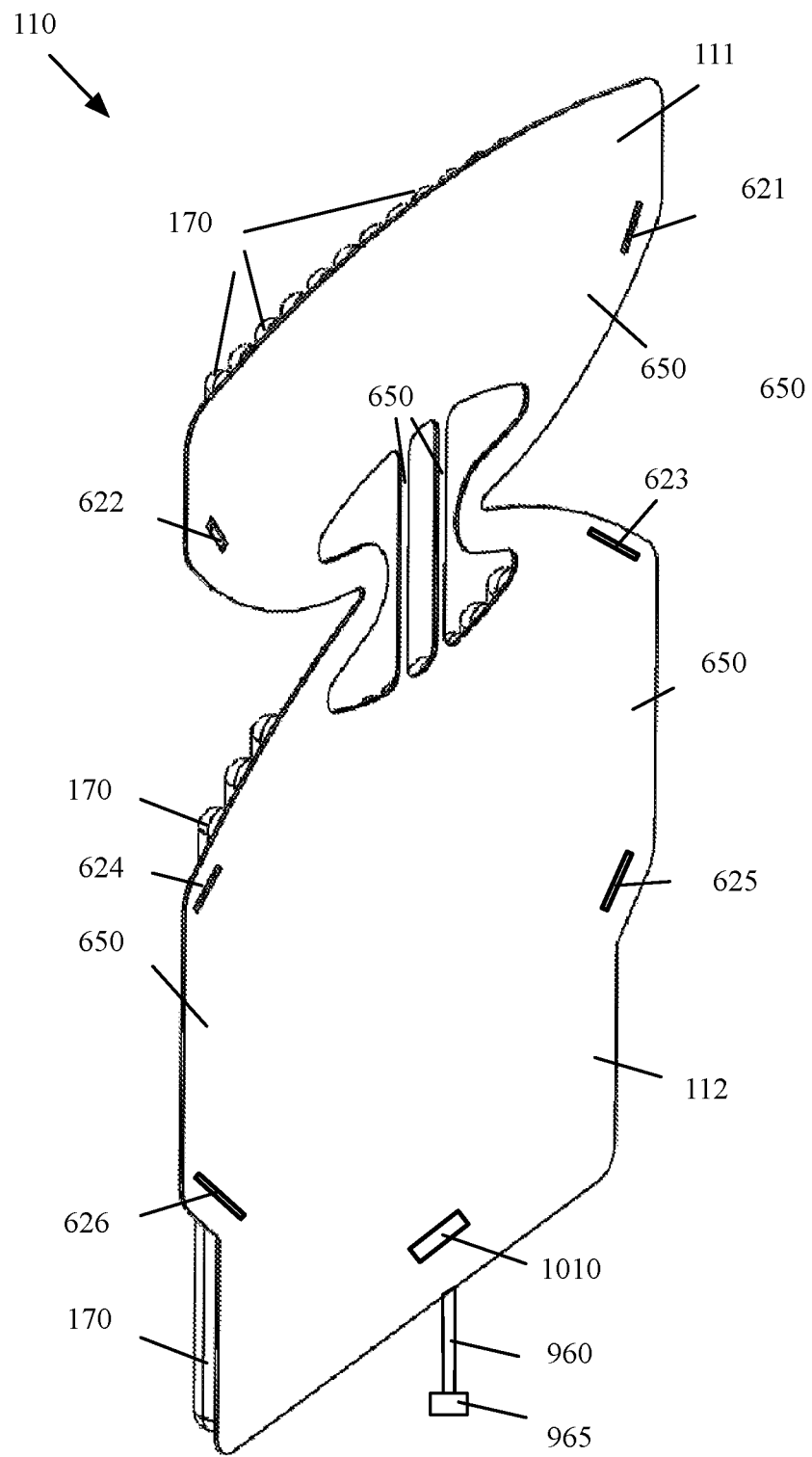
FIG. 10 is a back perspective view of the IV bag of FIG. 9, according to various aspects of the present embodiments.

With further reference to FIG. 9, the IV bag 110, in some embodiments, may be made by a process such as vacuum forming. Two pieces of plastic, for example, and without limitations, two pieces PVC may be used to form the IV bag during the manufacturing process. A front sheet 950 may be heated and the shapes of the fluidic channels 170 may be made by vacuuming the corresponding portions of the front sheet. A flat plastic sheet may then be sealed (e.g., by heating), as backing, to the front sheet 950 (FIG. 9). The two sheets may then be tripped to form the IV bag 110. FIG. 10 is a back perspective view of the IV bag of FIG. 9, according to various aspects of the present embodiments. With reference to FIG. 10, the backing 1010 may be a flat sheet of plastic that is sealed to the front sheet 950.

With reference to FIGS. 9 and 10, the IV bag 110 may include at least two pairs of slits 921-922 and 923-924 for stabilizing the shoulder section 111 and the arm section 112 when the IV bag is worn by a person. For example, FIGS. 1, 3, and 5 illustrate the strap 141 that is passed between the slits 921-922 and FIGS. 1, 2, and 5 illustrate the strap 142 that is passed between the slits 923-924.

It should be noted that the shoulder section 111 and the arm section 112 are connected to each other by one or more connectors 951 during the manufacturing. The front sheet 950, including the fluidic channels 170, the backing 110, and the connectors 951 form a unitary body. The connectors 951 are part of the IV bag 110, physically connect the shoulder section 111 and the arm section 112 together, provide stability, and provide comfort for the wearer.

The straps 141 and 142, on the other hand, are separate straps (e.g., made of rubber, fabric, plastic, etc.), and are used to provide additional stability when the IV bag 110 is worn. The arm section 112 may include the slits 925 and 925 for the band 143 (FIGS. 1-4) to secure the arm section 112 to the arm of the person.

In some embodiments, a near field communication (NFC) tag, a radio frequency identification (RFID) tag, and/or a bar code (e.g., and without limitations, a two-dimensional bar code) may be attached to the IV bag 110 (separate items which are collectively shown as item 1010 in FIG. 10 for clarity). The NFC tag 1010, the RFID tag 1010, and/or the bar code 1010 may include parameters and information about the fluid inside the IV bag 110, the delivery schedule and parameters, information about the person 190, certain restriction and conditions, etc.

Figure 11:
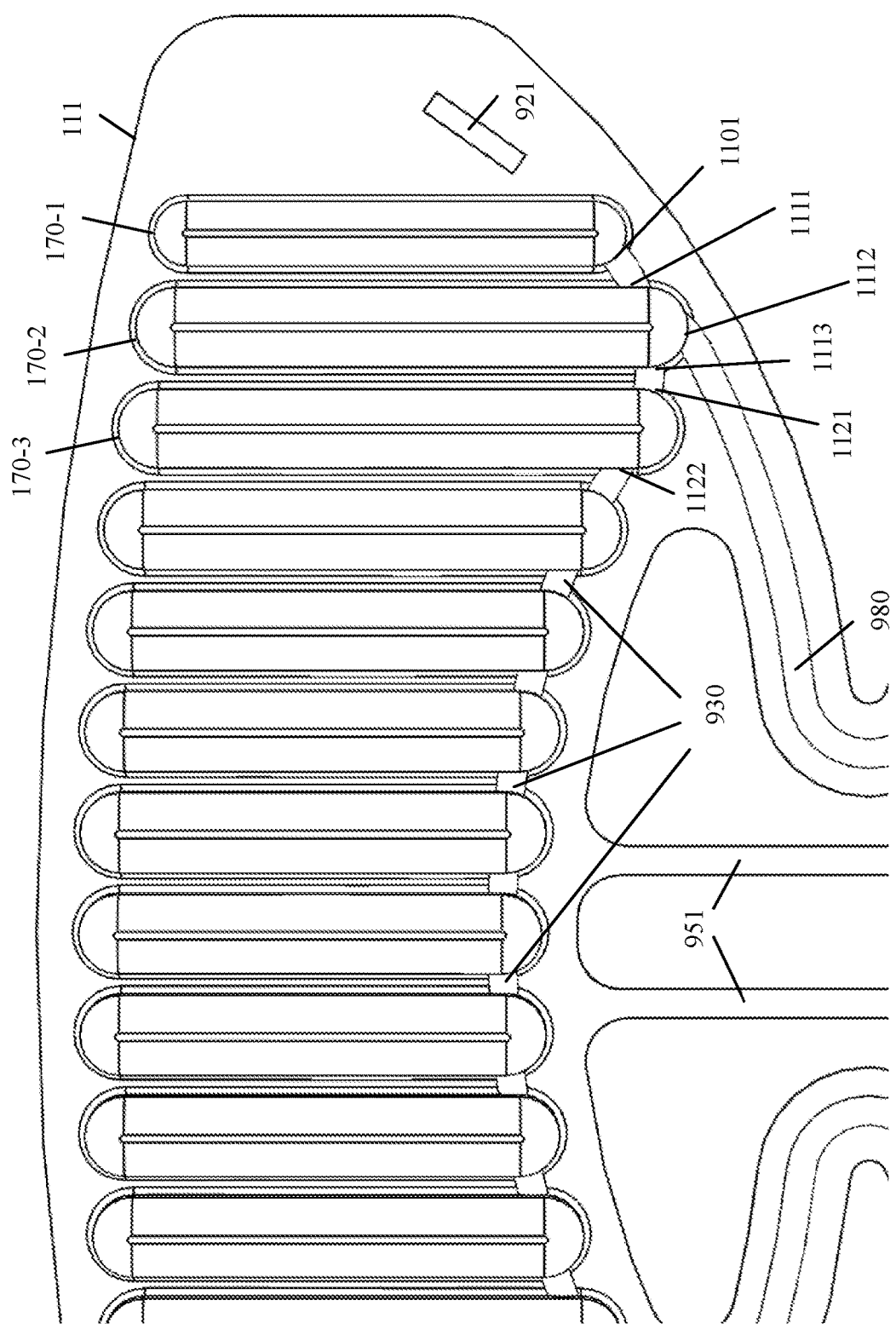
FIG. 11 is a front elevation view of a portion of the shoulder section of FIG. 9, illustrating the number of openings of different fluid channels, according to various aspects of the present disclosure.

Referring back to FIGS. 6-8, some of the fluid channels 170 may have a different number of openings 610 that the fluid channel depicted in FIGS. 6-8. FIG. 11 is a front elevation view of a portion of the shoulder section 111 of FIG. 9, illustrating the number of openings of different fluid channels, according to various aspects of the present disclosure. With reference to FIG. 11, the fluid channel 170-1 may include one opening 1101, the fluid channel 170-2 may include three opening 1111-1113, and the fluid channel 170-3 may include two opening 1121-1122.

FIG. 12 is a side perspective view of the IV bag 110 illustrating the approximate shape of the IV bag when it is worn on the shoulder and arm of a person, according to various aspects of the present disclosure. FIG. 13 is a side perspective view of an IV bag 110 of FIG. 12, illustrating the approximate shape of the IV bag when the person raises the arm, according to various aspects of the present disclosure.

With reference to FIGS. 12 and 13, the IV bag 110 is flexible to accommodate free movements of the hand. The IV bag 110, when filled with the fluid, has a small thickness (e.g., and without limitations between 0.1 to 0.8 inches) that may be comfortably worn under regular clothing.

As shown in FIGS. 9, 12, and 13, in any position, at least a subset of the fluidic channels 170 of the shoulder section 110 remain substantially parallel to each other and at least a subset of the fluidic channels 170 of the arm section 112 remain substantially parallel to each other. The IV bag 110 may be bent around the boundaries of the adjacent fluidic channels 170.

Figure 14:
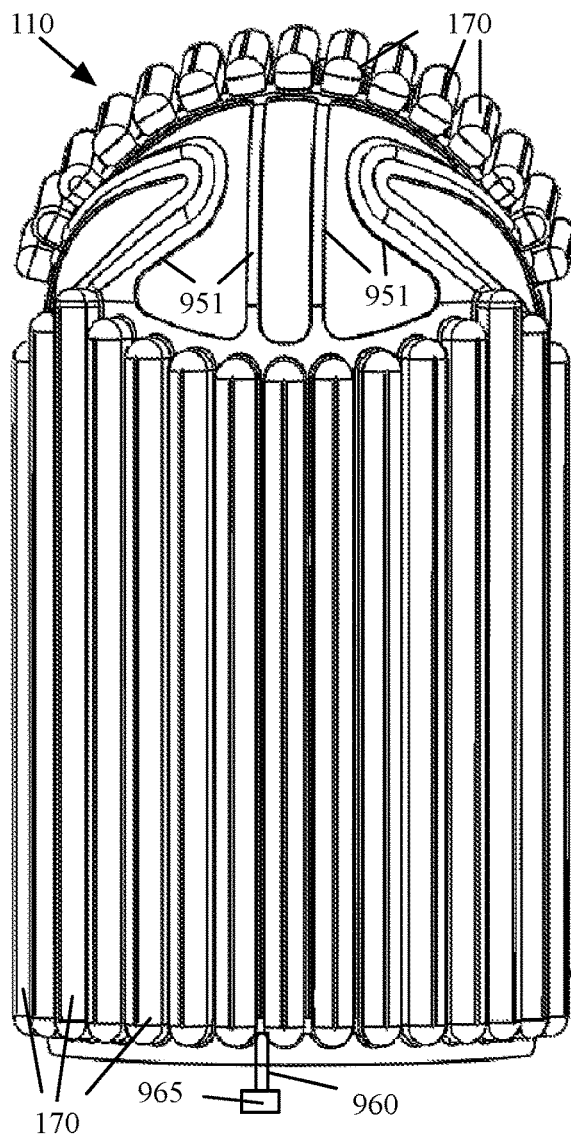
FIG. 14 is a side elevation view of the IV bag of FIG. 12, according to various aspects of the present disclosure.
Figure 15:
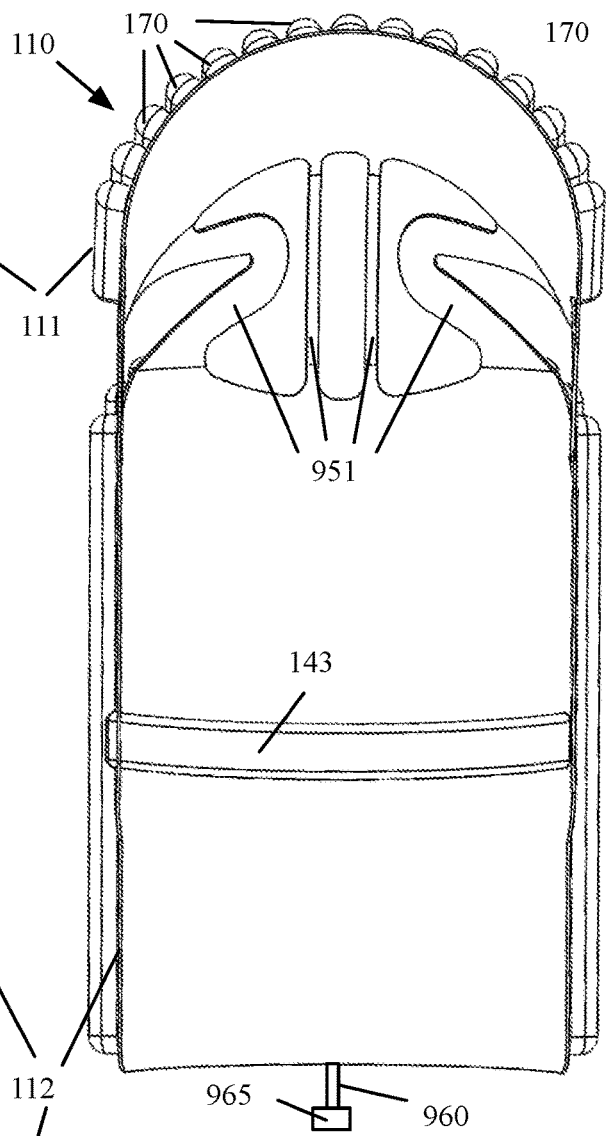
FIG. 15 is a side elevation view of the IV bag of FIG. 12 illustrating the interior of the IV bag, according to various aspects of the present disclosure.
Figure 16:
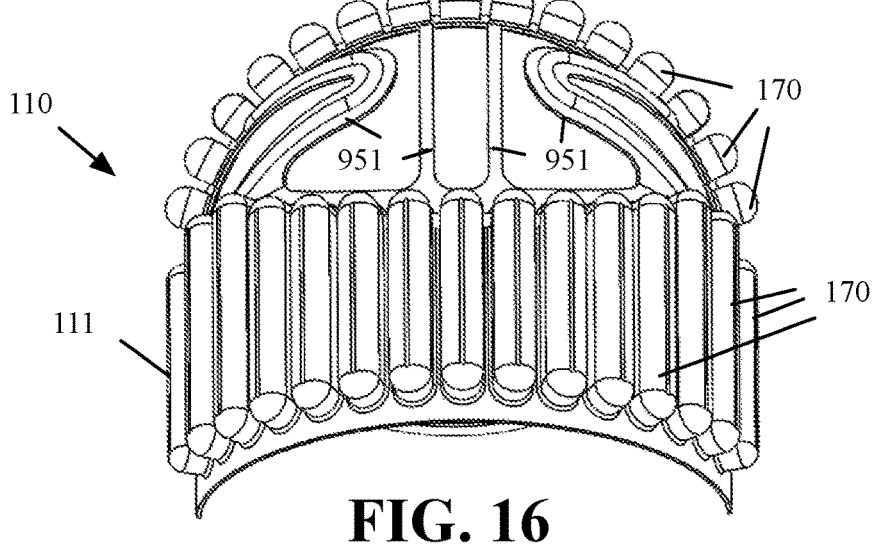
FIG. 16 is a top view of the IV bag of FIG. 12, according to various aspects of the present disclosure.

FIG. 14 is a side elevation view of the IV bag 110 of FIG. 12, according to various aspects of the present disclosure. FIG. 15 is a side elevation view of the IV bag 110 of FIG. 12 illustrating the interior of the IV bag, according to various aspects of the present disclosure. FIG. 16 is a top view of the IV bag 110 of FIG. 12, according to various aspects of the present disclosure. With reference to FIGS. 14-16, the IV bag 110, filled with fluid has the flexibility to bend around the arm and the shoulder of the person wearing the IV bag.

With reference to FIGS. 1-16, the many fluidic channels 170 on the shoulder section 111 and on the arm section 112 provide the technical advantage of the flexibility that is required to wear an IV bag on the shoulder and/or an arm of a person. The boundaries between the fluidic channels 170 provide many lines over which the IV bag 110 of the present embodiments may bend or curve to conform to the contours of a person's body.

The IV bag 110 may be connected to a fluid delivery device. FIG. 17 is a top perspective view of a fluid delivery device 120, according to various aspects of the present disclosure. FIG. 18 is the back perspective view of the fluid delivery device 120 of FIG. 17, according to various aspects of the present disclosure.

With respect to FIGS. 17 and 18, the fluid delivery device 120 may include a display 1710 and a housing 1740. The display 1710 may be, for example, and without limitations, a liquid crystal display (LCD) that may be used to display status and message. The display 1710, in some embodiments, may be a touch enabled display (e.g., a touchscreen) that may allow entering input and programming instructions through a user interface (UI).

The housing 1740 may include a base section 1750 and a door section 1760. The base section 1750 may include the slits 1820 and 1825 to allow the band 130 to be attached to the fluid delivery device 120. The base section 1750 may include a substantially flat surface 1810 to rest on a person's wrist after the band 130 goes around the person's wrist. The fluid delivery device 120 may include one or more batteries 1830 that, in some embodiments, may be located behind the flat surface 1810, inside the base section 1750. The one or more batteries may be rechargeable and/or replaceable. The one or more batteries may provide power to the electronic components of fluid delivery device 120.

Figure 19:
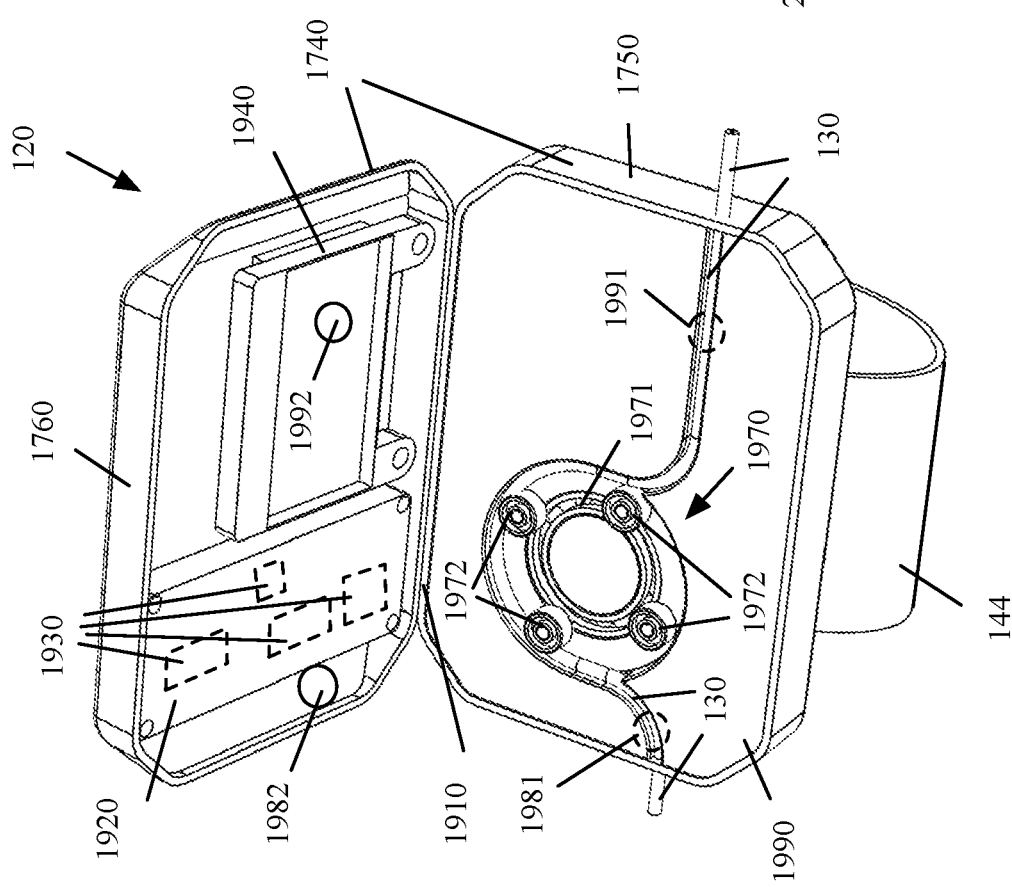
FIG. 19 is a top perspective view of the fluid delivery device of FIGS. 17 and 18, after the fluid delivery device's door is opened, according to various aspects of the present disclosure.

The fluid transfer tube 130 may go through the housing 1740 of the fluid delivery device 120. FIG. 19 is a top perspective view of the fluid delivery device 120 of FIGS. 17 and 18, after the fluid delivery device's door 1760 is opened, according to various aspects of the present disclosure. With reference to FIG. 19, the door 1760 may be opened around a hinge 1910. The fluid delivery device 120 may include a compartment 1920 to house one or more circuit boards 1930, a compartment 1940 to house the LCD display 1710, and a pump 1970.

The circuit board(s) 1930 may be, for example, and without limitations, printed circuit boards (PCBs). The circuit board(s) 1930 may include electrical components such as, for example, and without limitations, one or more processors, one or more memory units, etc. The circuit board(s) 1930, in different embodiments, may include components such as a global positioning system (GPS) receiver, wireless transceivers (such as Bluetooth transceiver, Wi-Fi transceiver, and/or cellular transceiver), one or more sensors (e.g., and without limitations, temperature sensors such as thermocouples and/or thermistors, heart rate sensors, etc.). The processor(s) may be microcontrollers, microprocessors, etc., that may control the pump 1970 to provide a programmable fluid delivery time. The memory unit(s) may store program(s) and/or data used by the processor(s).

The wireless transceiver(s) may be used to connect the fluid delivery device 120 to one or more external electronic devices, such as mobile electronic device, servers, etc., to send and receive data, to program the fluid delivery device 120, etc. The external electronic devices, in some embodiments, may use an application program that may be used to interface the external electronic devices with the fluid delivery device 120. The external electronic devices may be, for example, and without limitations, smartphones, tablet, computers, servers, etc. A GPS receiver integrated in the fluid delivery device 120 and/or a GPS receiver on a mobile device that is wirelessly connected to the fluid delivery device 120 may provide the information about the location where the fluid delivery.

The pump 1970, in some embodiments, may be a positive displacement pump. A positive displacement pump may move the fluid by repeatedly enclosing a fixed volume and moving it mechanically through the system. The pump, in some embodiments (such as the depicted embodiment), may be a peristaltic pump 1970. In other embodiments, the pump may another type of pump, such as, for example, and without limitations, a reciprocating pump, a rotary pump, etc.

Figure 20:
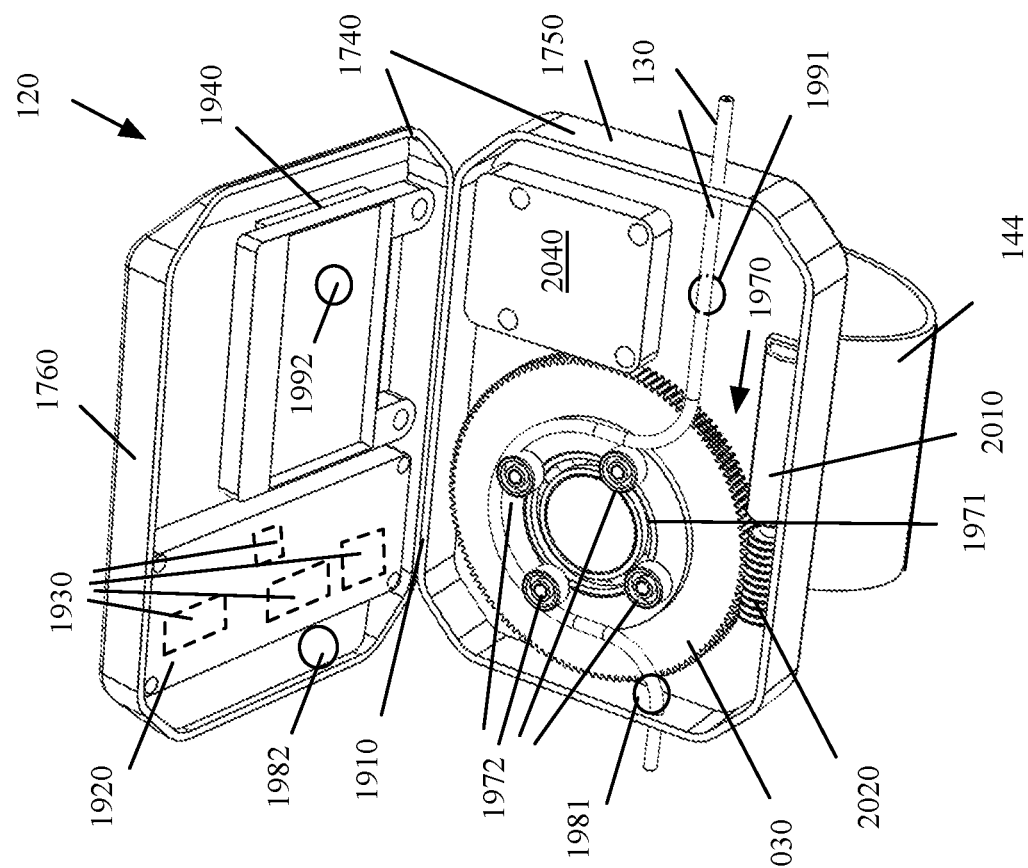
FIG. 20 is a top perspective view of the fluid delivery device of FIG. 19 after the base's cover is removed, according to various aspects of the present disclosure.

The base 1750 may include a cover 1990. FIG. 20 is a top perspective view of the fluid delivery device 120 of FIG. 19 after the base's cover is removed, according to various aspects of the present disclosure. With reference to FIG. 20, the battery charger 2040 may be used to charge the battery(ies) 1830 (FIG. 18). The peristaltic pump 1970 may include a rotor 1971, several rollers 1972, a motor 2010, a worm gear 2020, and a worm wheel 2030. the components of the peristaltic pump 1970 may be located inside a peristaltic pump housing (not shown). The electronic components that are in the base section 1750 and the door section 1760 may be communicatively coupled to each other (e.g., by one or more wires that may go through the hinge 1910). The battery(ies) 1830 (FIG. 18) may provide power to the electronic components located that are in the base section 1750 and the door section 1760. It should be noted that the specific locations of individual components of FIGS. 17-20 are exemplary, and the location of the fluid delivery device 120 components may be different, in different embodiments.

The peristaltic pump moves fluid through the tube 130 without the fluid to come in touch with any of the mechanisms of the pump. In contrast to the tube 130 and the IV bag 110 (FIG. 1) that are disposable, the fluid delivery device 120 may be reusable across multiple IV bags and tubes without any cross contaminations from the fluid. The IV bags 110 of the present embodiments may be prefilled (e.g., at a factory or at a distribution center) with specific fluid content. Each specific content may be used for a different intravenous therapy.

For each use, the tube 130 may be installed around the rollers 1972 of the pump 1970. The processor(s) of the fluid delivery device 120 may control the peristaltic pump 1970 by turning the peristaltic pump 1970 on or off. When the peristaltic pump 1970 is turned on, the motor 2010 may turn on and may rotate the worm gear 2020.

Some embodiments may provide control over the fluid delivery by controlling the peristaltic pump's motor. For example, the fluid delivery may be controlled (or programed) based on the revolutions per minute (RPM) of the peristaltic pump's motor 2010. For example, the processor(s) may control the fluid delivery by specifying the motor's 2010 RPM, and by setting the time duration of each fluid delivery period and the time duration of each fluid stoppage period. Alternatively, the processor(s) may control the fluid delivery by specifying the motor's 2010 RPM and by specifying the number of motor's revolutions for each fluid delivery period and the time duration of each fluid stoppage period.

In some embodiments, a user interface displayed on the display 1710 and/or a user interface displayed on the display of an electronic device that is wirelessly communicating with the fluid delivery device 120 may be used to provide the duration of each fluid delivery period, the duration of each fluid stoppage period, the number of motor's revolutions for each fluid delivery period and/or the time duration of each fluid stoppage period. In some embodiments, the user interface displayed on the display 1710 and/or the user interface displayed on the display of the external device may provide options to enter the fluid delivery rate (e.g., volume per unit of time). The processor(s) of the fluid delivery device 120 may then convert the time durations to the motor's 2101 RPM and/or to the motor's 2110 number of revolutions to control the peristaltic pump 1970.

The worm gear 2020 may rotate the worm wheel 2030 and the rotor 1971, which is connected to the worm wheel 2030. As the rotor 1971 rotates, the rollers 1972 may press against the tube 130, causing a positive displacement of the fluid towards the needle 160 (FIG. 1). When the processor(s) of the fluid delivery device 120 turn off the peristaltic pump 1970, the motor 2010 is turned off, causing the fluid in the tube to stop moving. The rollers 1972 prevent the fluid to move back from the direction of the needle 160 (FIG. 1) towards the IV bag 110.

Some embodiments may include one or more flow meters. In some embodiments, the flow meter(s) is/are optical flow meter(s). In the example of FIGS. 19 and 20, the fluid delivery device 120 may include two optical flow meters. The first optical flow meter that is in the input path of the fluid (the path before the fluid reaches the pump 1970), referred herein as the input flow meter, may include an optical source 1981 (e.g., a light emitting diode (LED) and optical sensor 1982 (e.g., a photo sensor). The second optical flow meter that is in the output path of the fluid (the path after the fluid leaves the pump 1970), referred herein as the output flow meter, may include an optical source 1991 and optical sensor 1922 (e.g., a photo sensor).

The optical source and the optical sensor of each optical flow meter may be located on the opposite side of the tube 130. In the depicted embodiment, the optical sources 1981 and 1991 are on the base section 1750, and the optical sensors 1982 and 1992 are on the door section 1760. In some other embodiments, the location of the optical source and the optical sensor of one or both optical flow meters may be different. For example, the optical source of one or both optical flow meters may be located on the door section 1760 and the corresponding optical sensor may be located on the base section 1750. In some other embodiments, the optical source and the optical sensor of each optical flow meter may be located on the base section 1750.

With further reference to FIGS. 19 and 20, the optical flow sensors may be used to monitor the flow in and out of the pump 1970. The technical advantage of an optical flow meter over other types of flow meters is that the optical flow meter may be integrated in the fluid delivery device 120 without coming in touch with the fluid, making the optical flow meters reusable.

Using the flow meters provides the ability to detect error conditions and to determine whether the fluid delivery device 120 is operating properly. The flow meters may also be used to monitor the amount of the fluid being delivered. If either the input flow meter or the output flow meter detect an interruption in the flow of the fluid for a certain duration of time (Tw) during a fluid delivery (a period where the pump 1970 is on), the interruption may indicate one of the following conditions: Detection of a bubble, the end of the delivery schedule, the entire fluid in the bag has been used, a malfunction in the IV bag 110 and/or the pipe 130 from the IV bag 100 to the fluid delivery device 120, and/or a malfunction in the peristaltic pump 1970. Under all these conditions, the drug delivery should be stopped. For example, the processor(s) of the fluid delivery device 120 may send one or more signals to the pump 1970 to stop the pump. The processor(s) may generate one or more audio visual alarm and/or may send one or more alert signal to one or more external device through the wireless transceiver(s).

The time Tw may be a programmable parameter and may typically be a small amount, for example, and without limitations, 500 milliseconds. If the input flow meter indicates a continuous flow during a fluid delivery period but the output flow meter indicates no flow for a certain time duration that is larger than a programmable time parameter Tpm, then there is a malfunction in the peristaltic pump. When this condition is detected by the processor(s), the processor(s) may send one or more signals to the pump 1970 to stop the pump. The processor(s) may generate one or more audio visual alarm and/or may send one or more alert signal to one or more external device through the wireless transceiver(s).

If both the input and output flow meters detect an interruption in the flow at the same time within a programmable time duration (e.g., a very short time window such as a few microseconds), then the condition indicates a loss of power to the pump or a mechanical malfunction causing the pump to stop. When this condition is detected by the processor(s), the processor(s) may send one or more signals to the pump 1970 to stop the pump. The processor(s) may generate one or more audio visual alarm and/or may send one or more alert signal to one or more external device through the wireless transceiver(s).

If the input flow meter detects a stop in the flow followed by the output flow meter detecting a stop in the flow within the time duration that it takes for the fluid to travel from the input flow meter location to the output flow meter location (Ttr) then the condition indicates the end of the fluid in the bag. This condition may be further verified from the expected end time of the delivery schedule which may be calculated from the parameters set in the fluid delivery device 120 before the fluid delivery starts. The time parameter Ttr may also be derived from the other parameters set in the fluid delivery device 12 and knowing the travel distance from the input flow meters to the output flow meter inside the fluid delivery device 120.

As described above with reference to FIG. 10, an NFC tag, an RFID tag, and/or a bar code may be attached to the IV bag 110 (collectively shown as 1010 in FIG. 10). The fluid delivery device 120, in some embodiments, may include an integrated reader for reading and writing NFC tags and/or RFID tags. The fluid delivery device 120, in some embodiments, may include an integrated reader (e.g., a camera and the associated software) for reading bar codes. The processor(s) of the fluid delivery device 120 may be configured to read the bag's NFC tag, RFID tag, and/or bar code, and automatically set the intravenous fluid delivery system's parameters according to the parameters read from the IV bag's NFC tag, RFID tag, and/or bar code.

In addition to, or in lieu of the IV bag having an NFC tag, an RFID tag, and/or a bar code, the fluid delivery device 120, in some embodiments, may include an NFC tag, an RFID tag, and/or a bar code (collectively shown as item 1880 in FIG. 18) which identify(ies) the characteristics and capabilities of the fluid delivery device 120. The processor(s) of the fluid delivery device 120, in some embodiments, may read the fluid delivery device's own NFC tag and/or RFID tag (or may read the bar cod through an external device), and may cross check the information and parameters read from the IV bag's NFC tag 1010, RFID tag 1010, and/or the bar code 1010 for security and compatibility and to prevent errors.

In the embodiments that the fluid delivery device 120 has ability to write into an NFC tag and/or into an RFID tag, the write function may be used to write back information into the fluid delivery device 120 NFC tag 1880 and/or RFID tag 1880. The write function may be used to write back information into the NFC tag 1010 and/or RFID tag 1010 of the IV bag 110 under password control if it is allowed to do so. In these embodiments, both the IV bag 100 and the fluid delivery device 120 may be updated with how they were used (e.g., the total delivery time, durations of individual fluid delivery periods and/or individual fluid stoppage periods, the total fluid delivery rate, the fluid delivery rate of individual fluid delivery periods, etc.) when and where they were used, etc. This information may also be communicated to a central database through the wireless connection, e.g., using an accompanying application program that may be used to control the fluid delivery device 120 operation.

Using the dual tag system described above along with the capability of the fluid delivery device 120 to read and write tags of both the IV bag and the fluid delivery device, and the wireless connectivity features of the fluid delivery device 120, numerous cross checking and device operation management features may be implemented particularly in hospitals and points of care settings.

Some embodiments provide the ability to prime the intravenous fluid delivery system 100 prior to injecting the fluid into a person's vein to prevent air from getting into the person's blood system. The air should be bled out of the fluid path prior to the start of fluid delivery into the person's vein. A user interface on the display 1710 and/or a user interface on a user interface displayed on the display of an electronic device that is wirelessly communicating with the fluid delivery device 120 may provide the selectable options to start, stop, reset, and/or prime the fluid delivery device 120. In addition to, or in lieu of the user interface options, some embodiments may provide physical buttons (or switches) on the housing 1740 of the fluid delivery device 120 to turn on (or off), start, stop, reset, and/or prime the fluid delivery device 120.

The physical on/off button may be used to manually turn on (or off) the battery(ies) power to the fluid delivery device 120. The user interface start option, or the physical start button, may be used to manually start (as opposite to starting by the processor(s) of the fluid delivery device 120) the fluid delivery by turning on the motor 2010 of the pump 1970.

In some embodiments, if the fluid delivery device 120 is not in operational mode for a threshold time duration Tnop, the fluid delivery device 120 may go into a sleep mode to conserve battery power. Pushing the physical start button and holding it for more than a threshold time duration Ts may wake up the fluid delivery device 120. Both the Tnop and Ts parameters may be programmable and may be stored in the fluid delivery device's 120 memory. Tnop may typically be on the order of several minutes (e.g., and without limitations, 20 minutes) and Ts may typically be on the order of a few seconds (e.g., and without limitations, 2 seconds). The sleep mode feature of the fluid delivery device 120 may be disabled, if desired, using another parameter that may be programmed and stored in the fluid delivery device's 120 memory. In some embodiments, the fluid delivery device 120 may need to be programmed to start at a certain time of the day in which case the processor(s) of the fluid delivery device 120 may disable the sleep function and may enable it back after the scheduled delivery is completed.

The user interface stop option, or the physical stop button, may be used to manually stop the delivery by turning off the motor 2010 of the pump 1970. The user interface reset option, or the physical reset button, may be used to manually reset the components of fluid delivery device 120 to an initial state.

The user interface options, or the physical buttons, may be used to prime the fluid delivery path of the fluid delivery device 120. For example, the start user interface start option, or the physical start button, may be selected (or activated) to start the pump 1970. The end of the tube 130 that is going to be connected to the needle 160 may be watched. When fluid starts flowing out of the tube 130, the stop user interface option and/or the physical stop button may then be selected (or activated) to stop the pump 1970. If the needle 160 is connected to the person's vein, the tube 130 may be connected to the needle 160, and the start user interface start option, or the physical start button, may be selected (or activated) to start the pump 1970 and start the delivery of the fluid.

Alternatively, the user interface prime option, or the physical prime button, may be selected (or activated) to start the pump 1970. When the fluid reaches the output flow meter described above, the processor(s) may receive one or more signals from the output flow meter indicating that the fluid has reached the output flow meter. The processor(s) may automatically stop the motor 2010 after a time duration which may be determined, for example, by the RPM of the motor 2010, to allow the fluid reach from output flow meter to the output of the tube 130. The processor(s) may generate an audio and/or a visual signal indicating that the intravenous fluid delivery system 100 is primed. If the needle 160 is connected to the person's vein, the tube 130 may be connected to the needle 160, and the start user interface start option, or the physical start button, may selected (or activated) to start the pump 1970 and start the delivery of the fluid.

Figure 21:
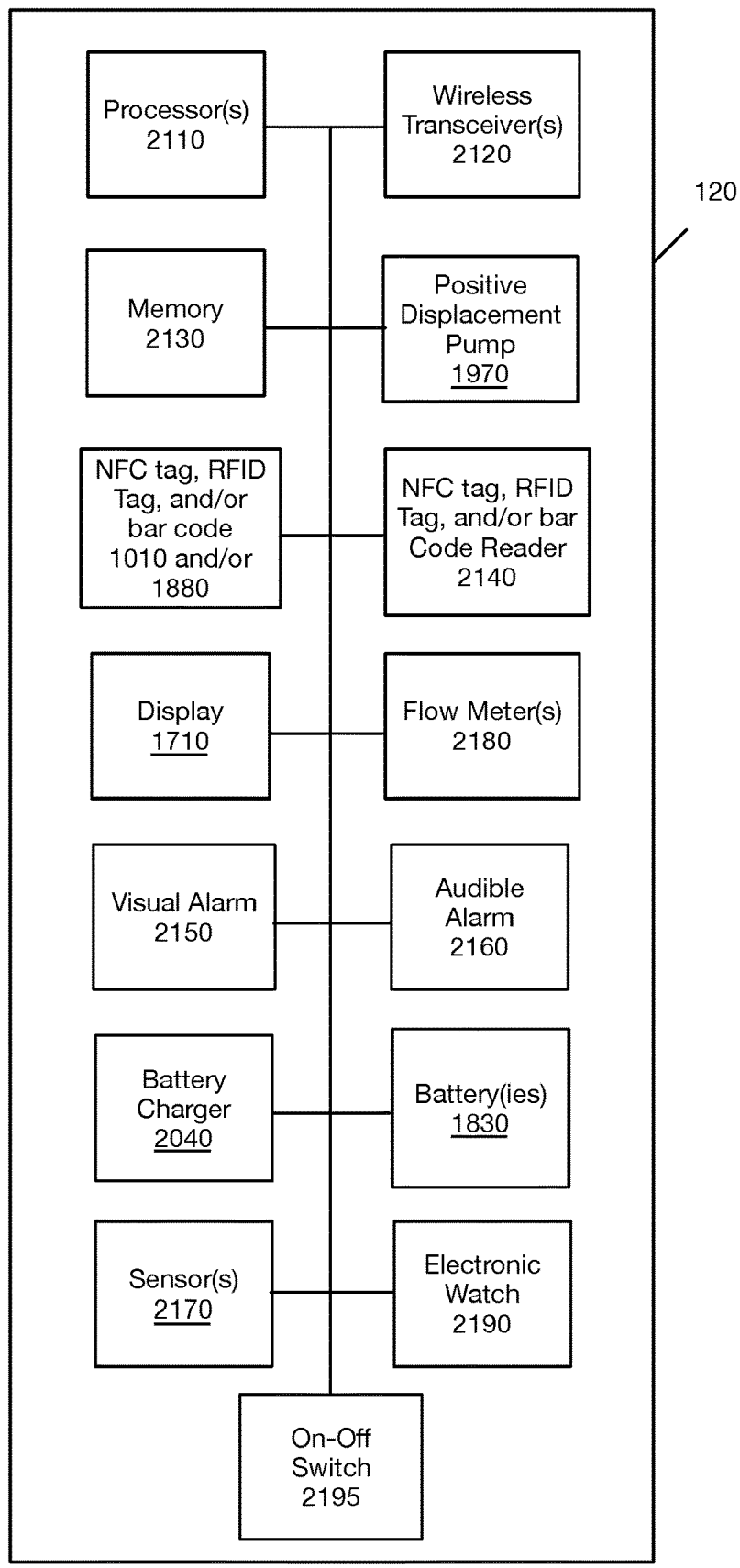
FIG. 21 is a block diagram illustrating the electronic and electromechanical components of fluid delivery device 120, according to various aspects of the present disclosure.

FIG. 21 is a block diagram illustrating the electronic and electromechanical components of fluid delivery device 120, according to various aspects of the present disclosure. As shown, the electronic components of the fluid delivery device 120 may include one or more processors 2110, one or more wireless transceivers 2120, one or more memory units 2130, a positive displacement pump 1970, an NFC tag 1010, an RFID tag 1010, and/or a bar code 1010 attached to the IV bag, an NFC tag 1880, an RFID tag 1880, and/or a bar code 1880 attached to the fluid delivery device, an NFC tag reader 2140, an RFID tag reader 2140, and/or a bar code reader 2140, a display 1710, one or more flow meter 2180 (e.g., the input and output flow meters described above with reference to FIGS. 19 and 20), a visual alarm 2150, an audible alarm 2160, a battery charger 2040, one or more batteries 1830, one or more sensors 2170, an electronic watch 2190, an/or on-off switch 2195.

Some of the functions of the processor(s) 2110, the wireless transceiver(s) 2120, the memory unit(s) 2130, the positive displacement pump 1970, the NFC tags (1010 and/or 1880), the RFID tags (1010 and/or 1880), the bar codes (1010 and/or 1880), the NFC reader 2140, the RFID reader 2140, the bar code reader 2140, the display 1710, the flow meters 2180, the battery(ies) 1830, and the battery charger 2040 were described above. It should be noted that the NFC reader, the RFID reader, and the bar code reader are separate readers, which are shown as one item in FIG. 21 for clarity.

The processor(s) 2110, in some embodiments, may generate an alarm when the processor(s) 2110 detect a malfunction in one or more components of the fluid delivery device 120. The processor(s) 2110 may report the alarms through one or more status lights (not shown), by audio signals through a small speaker (not shown), by displaying messages on the display 1710, and/or by sending one or more signals through the wireless transceiver(s) to external electronic devices, such as servers, mobile devices, computers, etc.

The sensor(s) 2170 may include sensors that are used to measure one or more vital signs of the person who is wearing the fluid delivery device 120. For example, and without limitations, the sensors may include body temperature sensors, oxygen sensors, heart rate sensors, motion sensors, blood pressure sensors, etc. The processor(s) 2110 may receive the sensor(s)' measurements and may generate an alarm if the measurements exceed one or more thresholds.

The sensor(s) 2170 may include sensors that are used to measure different environment and/or different parameters related to the fluid delivery device 120. For example, the sensor(s) 2170 may include air temperature sensors, atmospheric pressure sensors, accelerometers, magnetometers, gyroscopes, etc. The processor(s) 2110 may receive these sensor(s)' measurements and may generate reports and/or alarms based on the values of the measurements.

The fluid delivery device 120, in some embodiments, may include an electronic watch 2190. In these embodiments, the fluid delivery device 120 may function as a smart watch that may also be used to administer fluids to the wearer's vein. In some of these embodiments, the wireless transceiver(s) 2120 may include a cellular transceiver and/or a Wi-Fi transceiver that may allow the smart watch to be used as a smartphone to access cellular and/or Wi-Fi networks.

The fluid delivery device 120, in some embodiments, may include an on-off switch 2195. The on-off switch 2195 may be located on, or inside, the housing 1740 (FIG. 17) of the fluid delivery device 120. The on-off switch 2195 may be used to turn cut off the power from the battery(ies) to other components of the fluid delivery device 120.

Figure 22:
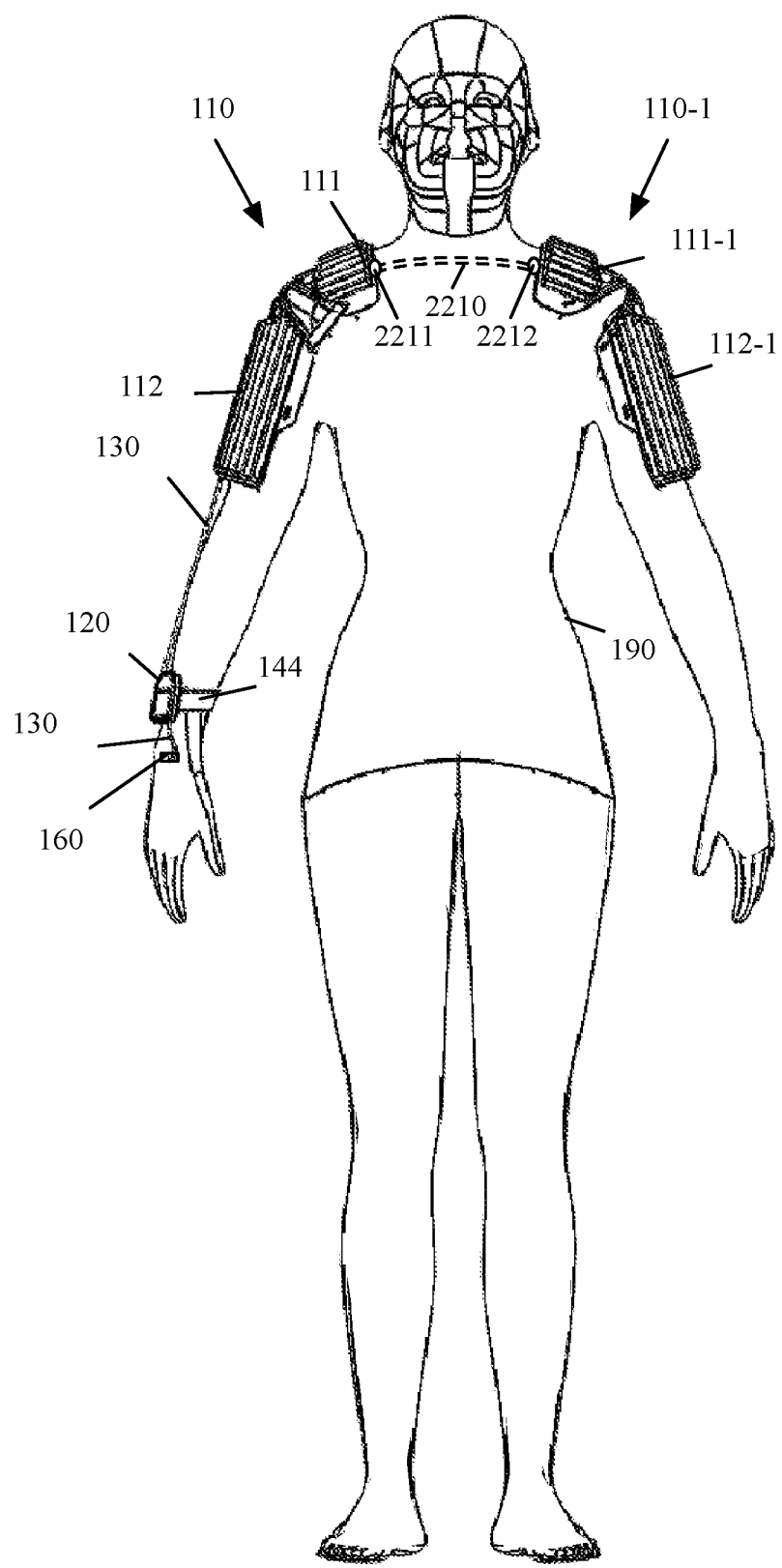
FIG. 22 illustrate a front perspective view of an example intravenous fluid delivery system that includes two fluidically connected intravenous bags that may be worn on both sides of the body, according to various aspects of the present embodiments.

Some embodiments may provide alternative intravenous fluid delivery systems. FIG. 22 illustrate a front perspective view of an example intravenous fluid delivery system that includes two fluidically connected intravenous bags that may be worn on both sides of the body, according to various aspects of the present embodiments.

With respect to FIG. 22, the intravenous fluid delivery system may include two IV bags 110 and 110-1 that may be worn on the opposite side of the body. The IV bag 110 may include a connector 2211, and IV bag 110-1 may include a connector 2212. The IV bags 110 and 110-1 of FIG. 22 may be substantially similar to the IV bag of FIGS. 1-5, except that the IV bag 110 of FIG. 22 is fluidically connected by a tube 2210, through the connectors 2211 and 2212, to the IV bag 110-1. The tube 2210 may connect the two IV bags 110 and 110-1 from the upper back of the person 190 (as shown), through the front upper torso, lower back, lower torso, etc. The contents of the two fluidically connected IV bags 110 and 110-1 may be administered through one fluid delivery device 120 and one needle 160.

With reference to FIGS. 1-5 and FIG. 22, the IV bag 110, in different embodiments, may include only the shoulder section 111, only the arm section 112, or both the shoulder section 111 and the arm section 112. With reference to FIG. 22, the IV bag 110-1, in different embodiments, may include only the shoulder section 111-1, only the arm section 112-1, or both the shoulder section 111-1 and the arm section 112-1.

The flexible IV bag 110 of the present embodiments may be configured to have two sections similar to the section 111 or to have two sections similar to the section 112 and be worn as a vest. The flexible IV bag 110 of the present embodiments may be configured to have one section similar to the section 111 or section 112 and be worn on the chest, on the abdomen, on the hip, on the thigh, or on the leg. The flexible IV bag 110 of the present embodiments may be configured to have one or more section similar to the section 111 and/or section 112 and be worn on an animal.

The electronic devices such as the portable intravenous fluid delivery device of the present embodiments, the electronic devices, the client devices, and/or the servers described above may include memory. The memory in the above examples may be one or more units of similar or different memories. For example, the electronic devices' memory may include, without any limitations, random access memory (RAM), read-only-memory (ROM), read-only compact discs (CD-ROM), erasable programmable read-only memories (EPROMs), electrically erasable programmable read-only memories (EEPROMs), flash memory (e.g., secured digital (SD) cards, mini-SD cards, micro-SD cards, etc.), magnetic and/or solid state hard drives, ultra-density optical discs, and/or any other optical or magnetic media.

Electronic devices described above may include one or more processing units. The processing unit may be a single-core processor or a multi-core processor in different embodiments. The electronic devices in some of the present embodiments may store computer program instructions in the memory, which may be a machine-readable or computer-readable medium (alternatively referred to as computer-readable storage medium, machine-readable medium, or machine-readable storage medium). The computer-readable medium may store a program that is executable by at least one processing unit and includes sets of instructions for performing various operations. Examples of programs or computer code include machine code, such as is produced by a compiler, and files including higher-level code that are executed by a computer, an electronic component, or a microprocessor using an interpreter. From these various memory units, the processing unit may retrieve instructions to execute and data to process in order to execute the processes of the present embodiments.

As used in this disclosure and any claims of this disclosure, the terms such as "processing unit," "processor," "controller," "microcontroller," "server", and "memory" all refer to electronic or other technological devices. These terms exclude people or groups of people. For the purposes of this disclosure, the terms display or displaying means displaying on an electronic device. As used in this disclosure and any claims of this disclosure, the terms "computer readable medium," "computer readable media," and "machine readable medium" are entirely restricted to tangible, physical objects that store information in a form that is readable by a processing unit. These terms exclude any wireless signals, wired download signals, and any other ephemeral or transitory signals.

In a first aspect, a wearable intravenous bag, comprises: a shoulder section comparing a plurality of fluidic channels, wherein the plurality of fluidic channels of the shoulder section are connected to each other through a first fluid passage, wherein the shoulder section is bendable at boundaries between adjacent fluidic channels of the arm section, wherein the shoulder section is configured to be placed over a shoulder of a person and to conform to contours of the person's shoulder; and an arm section comparing a plurality of fluidic channels, wherein the plurality of fluidic channels of the arm section are connected to each other through a second fluid passage, wherein the arm section is bendable at boundaries between adjacent fluidic channels of the arm section, wherein the arm section is configured to wrap around an arm of the person and to conform to contours of the person's arm; wherein the fluidic channels of the shoulder section and the fluidic channels of the arm section are connected to each other by: a set of one or more tubes that carries the fluid from the plurality of fluidic channels of the shoulder portion to the plurality of fluidic channels of the arm portion; and a set of one or more connectors; and wherein the shoulder section, the arm section, and the set of one or more connectors form a unitary body.

In an embodiment of the first aspect, each fluidic channel comprises one or more openings to fluidically connect the fluidic channel to other fluidic channels of intravenous bag.

In another embodiment of the first aspect, each fluidic channel has a width of between 0.1 to 0.8 inches and a length of between 1 to 9 inches.

In another embodiment of the first aspect, at least a subset of the fluidic channels of the shoulder section are substantially parallel to each other.

In another embodiment of the first aspect, at least a subset of the fluidic channels of the shoulder section remains substantially parallel to each other after the intravenous bag is bent around the adjacent fluidic channels of the shoulder section.

In another embodiment of the first aspect, at least a subset of the fluidic channels of the arm section are substantially parallel to each other.

In another embodiment of the first aspect, at least a subset of the fluidic channels of the arm section remains substantially parallel to each other after the intravenous bag is bent around the adjacent fluidic channels of the arm section.

In another embodiment of the first aspect, each tube in the set of tubes that carries the fluid passes through a connector in the set of one or more connector.

An embodiment of the first aspect further comprises a pair of slits on the arm section, the pair of slits configured to hold a strap to hold the arm section against the arm of the person.

Another embodiment of the first aspect further comprises further comprises one or more pairs of slits, each pair of slit comprising a slit located on the shoulder section and a slit located on the arm section, each pair of slits configured to hold a strap to connect the shoulder section to the arm section.

Another embodiment of the first aspect further comprises further comprises a fluid transfer pipe that carries the fluid from the plurality of fluid channels of the arm section to a fluid delivery device.

Another embodiment of the first aspect further comprises further comprises an injection port configured to receive a quantity of fluid other than the fluid inside the intravenous bag through one of a Y-set connector, a T-set connector, and a V-set connector.

In another embodiment of the first aspect, the wearable intravenous bag further comprises a connection configured to connect the wearable intravenous bag to another intravenous bag that is worn by the person.

In another embodiment of the first aspect, the fluid is one or more of a medication, a saline solution, a blood product, and nutrition.

In another embodiment of the first aspect, the shoulder section, the arm section, and the set of one or more connectors are made of polyvinyl chloride (PVC).

In another embodiment of the first aspect, the wearable intravenous bag is made from two sheets of plastic comprising a front sheet and a backing sheet.

In another embodiment of the first aspect, shapes of the fluidic channels are made by vacuuming the fluidic channels to form the corresponding shapes.

In another embodiment of the first aspect, the backing sheet is heat sealed to the front sheet.

Another embodiment of the first aspect further comprises a near field communication (NFC) tag storing parameters regarding at least one of the intravenous bag's fluid, a fluid delivery schedule, and parameters regarding the person.

In another embodiment of the first aspect, the NFC tag is writable, the NFC tag further storing parameters regarding at least one of a time that the intravenous bag was used, a location that the intravenous bag was used, and a set of fluid delivery parameters.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A wearable intravenous bag configured to hold a quantity of fluid, comprising:
    a shoulder section comprising a plurality of fluidic channels, wherein the plurality of fluidic channels of the shoulder section are connected to each other through a first fluid passage, wherein the shoulder section is bendable at boundaries between adjacent fluidic channels of the shoulder section, wherein the shoulder section is configured to be placed over a shoulder of a person and to conform to contours of the person's shoulder; and
    an arm section comprising a plurality of fluidic channels, wherein the plurality of fluidic channels of the arm section are connected to each other through a second fluid passage, wherein the arm section is bendable at boundaries between adjacent fluidic channels of the arm section, wherein the arm section is configured to wrap around an arm of the person and to conform to contours of the person's arm;
    wherein the fluidic channels of the shoulder section and the fluidic channels of the arm section are connected to each other by:
        a set of one or more tubes that carries the fluid from the plurality of fluidic channels of the shoulder section to the plurality of fluidic channels of the arm section; and
        a set of one or more connectors connecting the shoulder section and the arm section;
    wherein the shoulder section, the arm section, and the set of one or more connectors form a unitary body.

2. The wearable intravenous bag of claim 1, wherein each fluidic channel of the plurality of fluidic channels of the shoulder section and the arm section comprises one or more openings to fluidically connect the fluidic channel to other fluidic channels of the intravenous bag.

3. The wearable intravenous bag of claim 1, wherein each fluidic channel of the plurality of fluidic channels of the shoulder section and the arm section has a width of between 0.1 to 0.8 inches and a length of between 1 to 9 inches.

4. The wearable intravenous bag of claim 1, wherein at least a subset of the plurality of fluidic channels of the shoulder section are substantially parallel to each other.

5. The wearable intravenous bag of claim 1, wherein at least a subset of the plurality of fluidic channels of the shoulder section remains substantially parallel to each other after the intravenous bag is bent around the adjacent fluidic channels of the shoulder section.

6. The wearable intravenous bag of claim 1, wherein at least a subset of the plurality of fluidic channels of the arm section are substantially parallel to each other.

7. The wearable intravenous bag of claim 1, wherein at least a subset of the plurality of fluidic channels of the arm section remains substantially parallel to each other after the intravenous bag is bent around the adjacent fluidic channels of the arm section.

8. The wearable intravenous bag of claim 1, wherein each tube in the set of tubes that carries the fluid passes through a connector in the set of one or more connector.

9. The wearable intravenous bag of claim 1 further comprising a pair of slits on the arm section, the pair of slits configured to hold a strap to hold the arm section against the arm of the person.

10. The wearable intravenous bag of claim 1 further comprising one or more pairs of slits, each pair of slits comprising a slit located on the shoulder section and a slit located on the arm section, each pair of slits configured to hold a strap to connect the shoulder section to the arm section.

11. The wearable intravenous bag of claim 1 further comprising a fluid transfer pipe that carries the fluid from the plurality of fluidic channels of the arm section to a fluid delivery device.

12. The wearable intravenous bag of claim 1 further comprising an injection port configured to receive a quantity of fluid other than the fluid inside the intravenous bag through one of a Y-set connector, a T-set connector, and a V-set connector.

13. The wearable intravenous bag of claim 1, wherein the wearable intravenous bag further comprises a connection configured to connect the wearable intravenous bag to another intravenous bag that is worn by the person.

14. The wearable intravenous bag of claim 1, wherein the fluid is one or more of a medication, a saline solution, a blood product, and nutrition.

15. The wearable intravenous bag of claim 1, wherein the shoulder section, the arm section, and the set of one or more connectors are made of polyvinyl chloride (PVC).

16. The wearable intravenous bag of claim 1, wherein the wearable intravenous bag is made from two sheets of plastic comprising a front sheet and a backing sheet.

17. The wearable intravenous bag of claim 16, wherein the backing sheet is heat sealed to the front sheet.

18. The wearable intravenous bag of claim 1, wherein shapes of the plurality of fluidic channels of the shoulder section and the arm section are made by vacuuming the fluidic channels to form the corresponding shapes.

19. The wearable intravenous bag of claim 1 further comprising a near field communication (NFC) tag storing parameters regarding at least one of the fluid of the wearable intravenous bag, a fluid delivery schedule, and parameters regarding the person.

20. The wearable intravenous bag of claim 19, wherein the NFC tag is writable, the NFC tag further storing parameters regarding at least one of a time that the intravenous bag was used, a location where the intravenous bag was used, and a set of fluid delivery parameters.

* * * * *